(12) United States Patent
Breslauer et al.

(10) Patent No.: US 7,468,250 B2
(45) Date of Patent: *Dec. 23, 2008

(54) METHODS AND KITS FOR SCREENING NUCLEIC ACID DUPLEX STABILITY

(75) Inventors: Kenneth J. Breslauer, Edison, NJ (US); Craig A. Gelfand, Jackson, NJ (US); Eric G. Plum, Upper Arlington, OH (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 380 days.

This patent is subject to a terminal disclaimer.

(21) Appl. No.: 10/983,568

(22) Filed: Nov. 8, 2004

(65) Prior Publication Data

US 2005/0176032 A1 Aug. 11, 2005

Related U.S. Application Data

(63) Continuation-in-part of application No. 09/869,004, filed as application No. PCT/US99/30751 on Dec. 23, 1999, now Pat. No. 6,815,163.

(60) Provisional application No. 60/113,731, filed on Dec. 23, 1998, provisional application No. 60/119,909, filed on Feb. 12, 1999.

(51) Int. Cl.
*C12Q 1/68* (2006.01)

(52) U.S. Cl. .......................................... 435/6

(58) Field of Classification Search ........................ None
See application file for complete search history.

(56) References Cited

U.S. PATENT DOCUMENTS

| | | | | |
|---|---|---|---|---|
| 5,525,464 A | * | 6/1996 | Drmanac et al. | 435/6 |
| 5,532,129 A | * | 7/1996 | Heller | 435/6 |
| 5,616,465 A | * | 4/1997 | Lucas et al. | 435/6 |
| 5,972,612 A | | 10/1999 | Malmqvist et al. | 435/6 |
| 6,210,896 B1 | * | 4/2001 | Chan | 435/6 |
| 6,265,163 B1 | * | 7/2001 | Albrecht et al. | 435/6 |
| 6,815,163 B1 | * | 11/2004 | Breslauer et al. | 435/6 |

FOREIGN PATENT DOCUMENTS

| | | |
|---|---|---|
| EP | 0 745 690 A2 | 4/1996 |
| WO | WO 98/18965 | 7/1998 |

OTHER PUBLICATIONS

Tinoco, Jr. et al., "Principles and Applications in Biological Sciences", Physical Chemistry, pp. 451-453, (1978).*
Breslauer et al., "Predicting DNA duplex stabilitly from the vase sequence", Proc. Natl. Acad. Sci., vol. 83, pp. 3746-3750 (1986).*
Gelfand et al., "A quantitative method for evaluating the stabilities of nucleic acid", *Proc. Natl. Acad. Sci. USA* 1999 96:6113-6118.
Holbrook et al., "Enthalpy and heat capacity changes for formation of an Oligomeric DNA Duplex: Interpretation in terms of coupled processes of fomation and association of single-stranded Helices", *Biochemistry* 1999 38:8409-8422.
Olivas et al., "Competitive triplex/quadruplex equilibria involving guanine-rich oligonucleotides", *Biochemistry* 1995 34:274-284.
Morrison et al., "Solution-Phase Detection of Polynucleotides Using Interacting Fluorescent Labels and Competitive Hybridization", 1989 Analytical Biochemistry 183:231-244.

* cited by examiner

*Primary Examiner*—Kenneth R. Horlick
*Assistant Examiner*—David C Thomas
(74) *Attorney, Agent, or Firm*—Dann, Dorfman Herrell and Skillman; Robert C. Netter, Jr.; Kathleen D. Rigaut

(57) ABSTRACT

Simple methods and kits for determining the thermodynamic stability of nucleic acid duplexes and single polynucleotide polymorphisms via competitive equilibria are provided.

47 Claims, 1 Drawing Sheet

METHODS AND KITS FOR SCREENING NUCLEIC ACID DUPLEX STABILITY

This application is a continuation-in-part application of U.S. application Ser. No. 09/869,004, filed Jan. 24, 2002, now U.S. Pat. No. 6,815,163, which is a §371 application of PCT/US99/30751, filed Dec. 23, 1999, which claims priority to U.S. Provisional Application 60/113,731, filed Dec. 23, 1998, and U.S. Provisional Application 60/119,909, filed Feb. 12, 1999. The entire disclosure of each of the foregoing applications is incorporated by reference herein.

BACKGROUND OF THE INVENTION

Several publications and patent documents are cited throughout the specification in order to describe the state of the art to which this invention pertains. Each of these references is incorporated herein as though set forth in full.

Mutagenic lesions in DNA frequently result from structural modifications of the heterocyclic bases (exocyclic adducts, free radical-induced modifications) and/or from complete removal of the base (abasic sites). Further, cellular processing of lesion containing DNA can lead to mismatches, additions, deletions or base pair substitutions. Thus, by lesion, it is meant to include mismatches, additions and deletions. A wide range of lesion-induced thermodynamic effects have been observed. Typically, the free energy stabilizing the duplex is reduced significantly by inclusion of the lesion. Methods of determining lesion effects on duplex free energy are limited. Typically, the effect of a DNA modification on the energetics of duplex formation is measured by comparison of independently measured association constants for the modified and unmodified duplex or by comparing Tm values, which are commonly but erroneously believed to represent thermodynamic stability. Therefore, there is a need for a simple, reproducible and sensitive method for rapidly screening for duplex stability.

Typically, the effect of a DNA modification on the energies of duplex formation have been measured by comparison of independently measured association constants for the modified DNA and the unmodified duplex requiring two separate experiments.

Furthermore, there is a large technical barrier for direct measurement of single duplex association events. In conventional titration experiments, a solution of one strand is added to a solution of its complement with formation of a duplex monitored by any of a variety of methods, including spectroscopic and calorimetric methods. To extract useful information from a conventional titration, the experiment must be devised such that a significant fraction of free titrant will be present throughout the titration. Satisfaction of this condition leads to the familiar sinusoidal shape of the titration curve. To satisfy this condition, typically the product of the initial titrate concentration, c, and the association constant, K, is in the range 10<cK<1000. Due to the high association constant for nucleic acid duplexes, the component concentration must be below the association constant, accordingly, the components are likely to be too dilute to be detected by standard spectroscopic means.

A common spectroscopic method for monitoring duplex formation relies on the hyperchromicity of duplex formation. However, the extinction coefficients of duplexes of similar length is not a very sensitive reporter of the small differences in DNA content that are of most interest, as in the case of oligonucleotide duplexes with damage to only a single base. Even a technique such as circular dichroism is not sufficiently sensitive and also suffers from difficulties in interpretation of spectral variation which can be due to factors other than duplex formation.

SUMMARY OF THE INVENTION

An object of the present invention is to provide methods for screening for nucleic acid duplex stability by competitive equilibria. In these methods, a solution is first produced containing a known amount of an initial or reference nucleic acid duplex with a known stability. The initial duplex is comprised of a first nucleic acid strand having a sequence, wholly or in part, homologous to a target strand and a second nucleic acid strand having a sequence, wholly or in part, complementary to the target strand. A series of additions of target strand are then made by titrating the solution with a second solution comprising a known concentration of the target nucleic acid strand. This target nucleic acid strand competes with the first nucleic acid strand for binding to a nucleic acid strand of the initial nucleic acid duplex. After each addition or titration, the solution is subjected to conditions which disrupt some or all of the nucleic acid duplexes and triplexes in the solution and then subjected to conditions which promote duplex or triplex formation. Any changes in the amount of initial nucleic acid duplex formed as a function of the amount of target nucleic acid strand added are monitored. This method can be used for extracting enthalpy data by controlling temperature during duplex or triplex formation and monitoring changes as a function of temperature so that a family of titration curves can be made and used to extract enthalpy ($\Delta H^\circ$) data.

Another object of the present invention is directed to methods provide for detecting single nucleotide polymorphisms. In this embodiment of the invention, the initial nucleic acid duplex comprises a first and second nucleic acid strand, wherein the first or second strand of the duplex is designed to identify a single nucleotide polymorphism in a single- or double-stranded target nucleic acid sequence. In this method, the amount of the initial nucleic acid duplex in a solution is first determined. A fixed excess amount of a target nucleic acid strand is then added to the solution. The solution is then subjected to conditions which disrupt some or all duplexes or triplexes in the solution followed by conditions which promote duplex or triplex formation. The amount of initial duplex formed after addition of the target strand is then measured. This measured amount, after addition of the target strand, is indicative of the target strand containing the single nucleotide polymorphism.

Another aspect of the present invention includes methods for determining the concentration of a target nucleic acid strand which comprises adding a known volume and concentration of an initial nucleic acid duplex with a known stability to a known volume of a solution containing a target strand. Alternatively, a known volume of a solution of target strand can be added to a known volume of a solution containing a known concentration of an initial nucleic acid duplex with a known stability. The solution is then subjected to conditions which disrupt the initial nucleic acid duplex and any duplex between the target strand and a strand of the initial nucleic acid duplex, followed by exposure and conditions which promote duplex formation. The relative change in the amount of initial duplex formed in the solution after addition of the target strand is used to determine concentration of the target strand.

Methods are also provided for assessing stability of various selected target strands. In this method, competitive equilibrium assays are performed for each selected target strands with the same initial nucleic acid duplex. Changes in the amount of initial nucleic acid duplex formed as a function of the amount of the selected target nucleic acid strand added are compared for each target strand to ascertain differences in stability of duplexes or triplexes formed by the various target strands. In this embodiment of the invention, it is not necessary to know the stability of the initial nucleic acid duplex.

In a particular embodiment of the invention, the first nucleic acid strand of the initial duplex is labeled with a first member of a specific binding pair and the second nucleic acid strand of the initial duplex is labeled with a second member of the specific binding pair. In a particular embodiment of the invention, the specific binding pair is selected from the group consisting of antibody and antigen; enzyme and inhibitor; enzyme and coenzyme; and catalyst and inhibitor. In a particular embodiment of the invention, the specific binding pair is alkaline phosphatase and theophylline.

Yet another object of the present invention is to provide kits for screening for nucleic acid duplex stability and single nucleotide polymorphisms by competitive equilibria methods.

In yet another embodiment of the invention, methods are provided for screening for duplex stability by competitive equilibria, for detecting at least one single polymorphism, and for determining the concentration of a target molecule wherein molecules which are not nucleic acids are included in the initial nucleic acid duplex. For example, the stability of the binding of a protein for a particular nucleic acid sequence can be determined by employing an initial complex comprising a target nucleic acid and the protein and subsequently adding competitor nucleic acid of a different sequence. Similarly, the preference of nucleic acid binding proteins, such transcription factors, for particular nucleic acid sequences can be determined by these competitive equilibria.

DETAILED DESCRIPTION OF THE INVENTION

Figure 1:
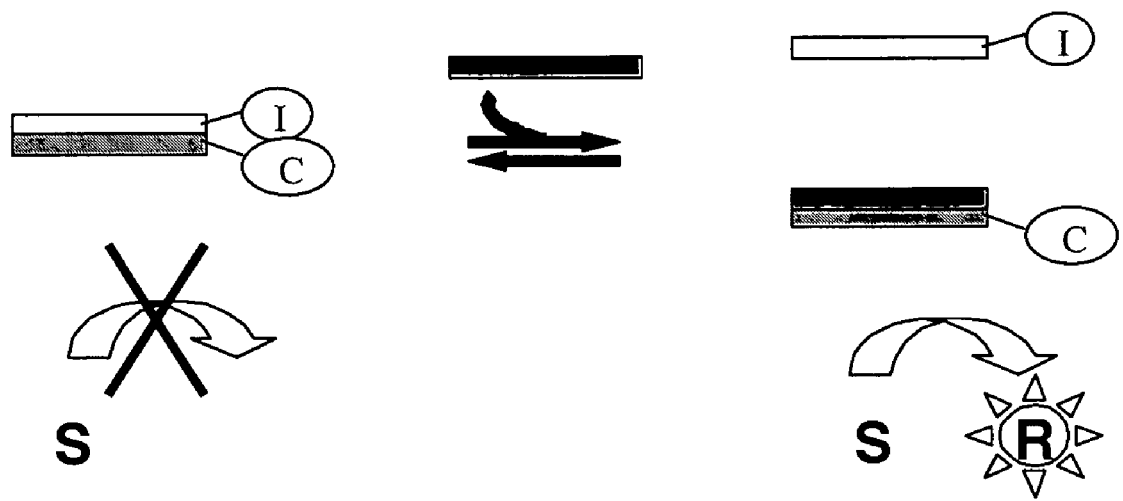
FIG. 1 is a schematic drawing demonstrating the use of a catalyst (C) and an inhibitor (I) pair to monitor the presence of a duplex. Black bar represents competitor strand. Substrate (S) can be converted to reporter (R) when catalyst is not blocked by inhibitor.

The present invention provides methods and kits for screening the impact of alterations in base structures (e.g., due to carcinogen exposure or synthetic modification); sequence context; and mismatched base pairs or bulged/unpaired bases on nucleic acid stability. Modifications of the phosphodiester backbone may also be detected. The small amounts of material required, speed of execution and applicability to a wide range of test strands make the assay useful for detailed thermodynamic characterizations and for screening applications. These features make the methods and kits of the present invention superior to calorimetry and other optical methods, with significant savings in the amount of test material necessary to perform a free energy determination. The range of effects on duplex stability of a particular defect or modification can be readily determined with the methods of the invention. With this information, the most interesting duplexes can be identified for further study. Thus, large investments in time and materials will be made only for systems of real interest.

The assays of the invention have at least two novel features which, when combined, provide a powerful and rapid method to assess the consequences upon duplex formation of perturbations to localized and/or global chemical features of nucleic acids. The first unique aspect is using two simultaneously competing equilibria to identify differences in equilibrium constants, between formation of two different nucleic acid duplexes. A second novel feature of the present invention is that these assays are performed simultaneously, thus requiring only one experiment.

Having nucleic acids compete for duplex formation, as in the present method, creates a second equilibrium, referred to herein as a "competition" for duplex formation, that is measurable at essentially any concentration range. Thus, the concentrations can be tailored to virtually any method of detection. Further, the competition is measured directly from a single experiment rather than having to compare the results of two independently measured experiments.

Another innovative aspect of this invention is the ability to discriminate between the two duplexes being formed. In one embodiment of the present invention fluorescence energy transfer (FET) is used to facilitate this discrimination. FET provides a unique, extremely sensitive, and essentially binary means of discrimination because only a duplex with both the donor and acceptor dyes will have the spectroscopic signature of the energy transfer.

Competitive equilibrium assays of the present invention are more widely adaptable to a variety of nucleic acid systems than are assays that are based on changes in intrinsic spectral characteristics of the dyes. For example, the FET assay of the invention is dependent only on the presence of the two dyes and is limited only by the necessity of modifying DNA to bear the dyes and the fact that the distance between the dyes increases substantially when the initial FET duplex is disrupted. Any spectral changes that accompany the disruption of the FET duplex can be easily treated during data analysis and do not cause any significant complication for the FET assay. Thus, the present invention has a number of significant advantages over prior art techniques for determining duplex stability.

One of the key features of the invention is the flexibility in the nature of the test nucleic acid components that can be evaluated. In one experiment, two 13 mer DNA oligonucleotides, each bearing one of the FET fluorophores, referred to herein as donor (D) and acceptor (A) strands, form a duplex. The test or target strand competitor is a third DNA oligonucleotide of the same length bearing a single damaged site at the central position. However, application of the method is general, encompassing virtually any variation in the nature of the nucleic acid duplex and test strand competitor. The donor (D) and acceptor (A) strands need not be the same length nor must the target, whether single strand or duplex. Further, as used herein, the terms "DNA", "nucleic acid", "oligonucleotide" and "strand" are meant to include other variations as there is no requirement for any of the three nucleic acid strands to be DNA. Accordingly, the terms "DNA", "nucleic acid", "oligonucleotide" and "strand" are meant to include DNA, RNA, and analogues including those comprised, in whole or in part, of modified bases and/or modified backbones such as peptido-nucleic acids (PNA) and other oligomers, incorporating modified phosphate and/or sugar moieties (e.g. PNAs, methyl phosphonates, phosphorothioates) that maintain duplex-forming ability may be used in the method of the invention. Further, these terms are also inclusive of the vast number of non-Watson-Crick nucleotide base variations that may be incorporated into any of the components, including intra strand crosslinks, abasic sites, naturally occurring or synthetic base variants, base mimetics and base adducts, including, for example, carcinogen-induced adducts. There is also no need to limit the system to three independent strands of the same length competing for formation of two possible duplexes.

Most nucleic acid amplification techniques, such as polymerase chain reaction produce duplex target. The technique of the present invention can be used on such targets in one of two ways.

In a first embodiment, the stability of the "third" strand of a DNA triplex can be determined. A triple helix is formed between the target duplex and one of the strands of the reference duplex. The sequence requirements for triple helix formation are well known. Typically, triple helices involve stretches of pyrimidines on one strand of a Watson-Crick duplex, a complementary stretch of purines on the other strand of the Watson-Crick duplex, and a third strand comprised of stretches of either complementary purines or pyrimidines which resides in the major groove of the duplex. Details of the sequence requirements and tolerated substitutions are well known and widely described in the art. The target duplex need not be disrupted and all calculation equations provided in the Examples are applicable to this embodiment without modification.

The second embodiment is more complex and applicable only when sequences do not meet the requirements for triple helix formation. In this embodiment, the target duplex must be disrupted, i.e. melted, so that both the donor-labeled and acceptor-labeled oligonucleotide can bind to the complementary strand of the target duplex. The addition of two equilibria (the formation of the target duplex and the interaction of the donor strand with one of the target duplex strands) makes this formalism inappropriate for deriving quantitative data. However, due to the law of mass action, the equilibrium distribution of complexes will still depend on the relative values of the equilibrium association constants and the various concentrations. Therefore, the FET observable will also depend on these values. As a consequence, qualitative information on the relative stability of complexes formed by the target duplex's component strands and various sets of DNA duplex probes can be obtained.

The method is also useful for structures that might include large bulging/unpaired regions, competing internal loops and/or hairpins or other deviations from simple duplex formation. The above-mentioned variants may occur in combination, thereby increasing the number of potential targets of study.

The only limitations are that the FET donor and acceptor be within resonance distance in the initial duplex and that formation of the competing complex prevents energy transfer by displacement of either donor or acceptor. Any FET donor and acceptor pair can be used and such dyes are well known in the art and commercially available. The fluorescent dyes may be at opposite ends of the duplex (5' and 5' or 3' and 3'), the same end of the duplex (5' and 3'), or with one or both fluorophores in the interior of the strand(s). The fluorophores may be linked after oligonucleotide synthesis or, when the phosphoramidites are available, incorporated during synthesis.

Further, FET, monitored either by fluorescence of the acceptor or by quenching of the donor, is not the only usable means of monitoring the amount of the reference or donor-acceptor duplex. Any method by which the amount of reference or initial duplex can be monitored as a function of the amount of target can be used. Eximer fluorescence or other optical means can be used. In fact, nucleic acid strands of the initial duplex can be labeled with any pair of species with properties or characteristics dependent upon proximity, such as, for example, fluorescent dyes. Further, if the assay is carried out on a surface, surface plasmon resonance (SPR) spectroscopy may be employed with the label being a chromophore at the wavelength used in the SPR measurement. Alternatively, the alternative competing strands could each bear a different chromophore, giving a positive signal for each alternative duplex, and allowing simultaneous monitoring of both duplexes with positive signals.

As another alternative to FET monitoring, the initial duplex can be labeled with specific binding pairs and employed in the methods of the instant invention. As used herein, the term "specific binding pair" refers to a pair of molecules that specifically bind to one another. Each specific binding pair comprises two members, however, it may be possible to find additional compounds that may specifically bind to either member of a given specific binding pair. Examples of specific binding pairs include, but are not limited to, antibody-antigen pairs, enzyme-inhibitor pairs (e.g., catalyst-inhibitor pair), and enzyme-coenzyme pairs. Members of the specific binding pairs should be stable under the conditions of the experiment. Furthermore, the attachment of the specific binding pair to the initial duplex should allow for their productive interaction when the initial duplex is intact. Varying the length of the linker may allow for more productive interactions. Methods of coupling proteins and small molecules to oligonucleotides are well known in the art (see, e.g., Thuong and Asseline (2000) Current Protocols in Nucleic Acid Chemistry, 4.2.1-4.2.33; Davies, M. J., et al. (2000) Chem. Soc. Rev. 29:97-107). Due to incomplete conjugation or improper conjugation, a subpopulation of specific binding pair-oligonucleotide complexes may exist wherein the specific binding pair does not interact. The contribution of such a subpopulation to the output signal, however, will become part of the background, if small, and/or can be corrected by comparison with control experiments. Additionally, when the antigen-antibody binding pair is employed, titration may be an issue as very strong interactions may lead to kinetic traps, preventing titration equilibrium from being achieved at a sufficiently rapid rate. The addition of detergents, salts, chaotropes, or other agents that can reduce the antigen-antibody overall interaction energy may be added to the reaction mixture. Assuming that all of the competing complexes are similarly affected by these agents, the kinetic trap issue can be overcome. Indeed, the use of these additives to modulate AG, in order to find a more accessible titration range for LAG can be employed in any of the methods of the instant invention even when the antibody-antigen binding pair is not employed.

The presence and disruption of initial duplexes labeled with specific binding pairs can be monitored by a variety of methods. For example, a catalyst can be conjugated to one strand (this conjugate is designated C and is analogous to D in the FET experiments) and an inhibitor can be conjugated to the complementary strand (this conjugate is designated I and is analogous to A in the FET experiments). The positioning of the catalyst and inhibitor should be such that when the duplex is intact, the activity of the catalyst will be inhibited. Upon disruption of the duplex, by competition with the competing oligonucleotide, the catalyst will be freed to catalyze the conversion of a substrate (S) to a reporter (R) which can be monitored (see FIG. 1). The production of a signal, after a given time, or the rate of production of that signal can provide a measure of the concentration of free catalyst-oligonucleotide conjugate, and thus a measure of intact reference duplex. The analysis of the resultant data, e.g. the concentration of added competitor vs. fraction of intact reference duplex, can be analyzed identically to the FET monitored titrations as described hereinbelow.

Indeed, due to the strong binding of the oligonucleotides of the reference duplex coupled to the catalyst and the inhibitor, the effective inhibitor concentration approaches infinity. This has two effects: 1) even a relatively poor inhibitor will suffice and 2) the catalyst engaged in the inhibitor complex can be treated as if it is absent from the solution. The substrate will be present in saturating quantities, ensuring the maximum possible turnover and pseudo first order kinetics. Thus, the measured rate, r, corresponds to $V_{max}$ in conventional enzyme kinetics notation.

$$r = \frac{d[R]}{dt} = k[CS] = k[C]$$

It is reasonable to assume that the pseudo first order rate constant k does not depend on the concentration of uninhibited catalyst or the concentration of the of added competing stand, so the ratio of r to $r_{max}$ (measured in the absence of inhibitor-oligonucleotide complex) is related to the value previously defined for the FET monitored experiments.

$$\frac{r}{r_{max}} = \frac{k[C]}{k[C]_t} = \frac{[C]}{[C]_t}$$

Since $$\theta = \frac{[C]_t - [C]}{[C]_t}, \quad \theta = 1 - \frac{r}{r_{max}}$$

The experiment can be repeated as a function of $[X_t]$. The analysis of the resultant $\theta$ vs. $[X_t]$ or $\theta$ vs. log $[X_t]$ curves to extract thermodynamic parameters is unchanged.

The information content of the proposed procedure is identical to that developed for stability measurements using FET detection. There are, however, some significant differences in the execution of the procedure. The primary difference is that the detection requires addition of the substrate subsequent to establishment of the competitive equilibrium. As a consequence, typical embodiments will require that each point in a titration must be determined in separate solutions; serial additions of substrate are not possible. This will not present a significant impediment to implementation of the method. The greatly enhanced sensitivity and the potential for execution of the experiment in microwell plates with simultaneous detection of the entire titration curve, overwhelm any disadvantages introduced by loss of the ability to conduct a single vessel titration.

As an alternative to these separate end-point titrations, limiting and fully consumed amounts of a substrate may be added at each point along the titration, after equilibrium of the competing molecules is achieved. For example, a chemiluminescent substrate could be added, and the rate of light generation could be measured, until the substrate is completely consumed. Thus, signal is generated, but never builds up beyond detection limits of the instrument, and the rate of the enzyme reaction becomes the indicator for the amount of AX complex at each point in the titration. There could be limitations in the build up of chemiluminescence reaction products, which could eventually inhibit the chemiluminescent reaction by simple equilibrium, but these effects can be measured and corrected, and/or other biochemical processes can be added to remove the build up of reaction products. Such methods are known in the field. For example, the technique of pyrosequencing (Biotage, Uppsala, Sweden) for DNA sequencing uses a similar approach of chemiluminescence between single-base DNA polymerase extension steps (see www.pyrosequencing.com/pages/technology_content).

The high throughput nature of this assay, in comparison to the more time and material intensive techniques generally used for thermodynamic analysis, makes the assay applicable to various problems in biotechnology and pharmaceutical research. For example, this assay can be used to evaluate nucleotide mimetics as drugs such as the anti-HIV drugs ddC and AZT; to evaluate the effects of carcinogen/chemical exposure on the stability of DNA and DNA-RNA hybrid duplexes; and for screening of various parameters for hybridization studies (e.g. temperature, buffer, sequences). Screening of non-natural nucleic acid analogs as antisense or antisense agents, or active expression antagonists such as small interfering RNA (siRNA or RNAi), can also be addressed by this method. The assay of the invention can be a companion technique to help improve existing hybridization techniques. The method of the invention can also be used for screening, in solution, for the presence of single nucleotide polymorphisms (SNPs or "snips") which are used in pharmacogenetic research targeted at identifying the genetic basis of disease and genetic diagnosis of the potential for such disease predisposition in individuals. The latter aspects have particular importance in the biotechnology industry. Many companies are currently involved in developing and marketing hybridization assays for a wide variety of research and development efforts. Virtually all of the assays currently in use rely on immobilization of at least one participant in the hybridization reaction. Significantly, the immobilization introduces a host of complications, including non-specific interaction of any/all of the components with the immobilizing platform; possible distortion of the biochemically important equilibrium due to immobilization; the possibility that the chemical linkage of the immobilization can partially occlude the necessary interactions with the non-immobilized components; and the necessity of additional steps in the protocol for the immobilization itself prior to running the binding experiments. The method of the invention, with the capacity of being performed entirely in solution, eliminates the complications caused by immobilization. Further, because the method uses titration, control experiments with standardized DNA can be run frequently or in parallel with test compounds to eliminate spurious results. Such standardized DNA is a component of a kit for carrying out the method of the invention.

The competing equilibria which are the basis of this assay provide a greatly enhanced method for detecting differences in stability between two nearly identical duplexes. Studying the association of two strands forming one duplex and comparison of the association of two other strands in a separate experiment, as is done in current methods, requires two experiments with the inherent compounding of experimental error. The present invention advantageously requires only one.

The calculations used for data analysis are derived from the general equations for three component, two-equilibria systems as taught by Linn and Riggs (J. Mol. Biol. (1972), 72, 671-90).

Two equilibrium association constants are defined below, with subscripts f and t indicating free and total concentrations, respectively, and AD, AX, D, A, and X represent the donor/acceptor complex, the competitor/acceptor complex, donor strand, and acceptor strand, and the competitor or "test" strand, respectively:

$$K_{AX} = \frac{[AX]}{[X]_f [A]_f}$$ (Equation 1)

$$= \frac{[AX]}{([X]_t - [AX])([A]_t - [AD] - [AX])}$$

$$K_{AD} = \frac{[AD]}{[D]_f [A]_f}$$ (Equation 2)

$$= \frac{[AD]}{([D]_t - [AD])([A]_t - [AD] - [AX])}$$

These equations are for the "test" or "target" strand forming a complex with the acceptor strand. In this and the models that follow, the opposite competition, with X binding to D, can also be described by simple substitution of the terms.

These basic expressions for the equilibrium constants can be combined and rearranged to the following equation:

$$[AD] = \frac{[A]_t([D]_t - [AD])}{1 + \frac{([X]_t - [AX])K_{AX}}{K_{AD}} + ([D]_t - [AD])}$$ (Equation 3)

The loss of energy transfer is monitored as the AD complex is disrupted by the formation of AX. The complementary measurement of emission of the acceptor subsequent to energy transfer also may be used. Which approach works better will depend on the photophysical properties of the fluorescent dyes. As discussed, the value, θ is the fraction of the initially observed fluorescence energy transfer at each point in the titration and is related to the relative concentrations of the donor/acceptor complex ([AD]) to [total donor strand] ([D]$_t$) ([AD]=[D]$_t$ at the beginning of the titration):

$$\theta_n = \frac{[AD]}{[D]_t} = \frac{I_D - I_n}{I_D - I_{AD}}$$ (Equation 4)

with relative fluorescence readings for the dilution-corrected relative fluorescence at each point n, $I_n$, fluorescence of the fully formed FET duplex, $I_{AD}$, and the fluorescence of the donor strand alone, $I_D$.

In equation 5, the dilution corrections are added explicitly, where $V_o$ is the initial volume of the D-containing solution, $V_A$ is the volume of the added A-containing solution, and $V_i$ is the volume of the ith aliquot of the X-containing solution.

$$\theta_n = \frac{I_D - I_n\left(\frac{V_o + V_A + \sum_{i=1}^{n} V_i}{V_o}\right)}{I_D - I_{AD}\left(\frac{V_o + V_A}{V_o}\right)}$$ (Equation 5)

Substituting Equation 3 into Equation 4, assuming that [X]$_t$>>[AX], and rearranging yields Equation 6.

$$\theta = \frac{[A]_t(1-\theta)}{\frac{1+[X]_t K_{AX}}{K_{AD}} + [D]_t(1-\theta)}$$ (Equation 6)

A program (written in the Microsoft VBA language) that computes a function theta ([A]$_t$, [D]$_t$, [X]$_t$, K$_{AD}$, K$_{AX}$) to calculate the isotherms (θ vs. X$_t$ or log X$_t$) using equation 6 is depicted in Example 5. The value of θ is found by iteration to satisfy the equation RHS (equation 6)−θ=0, where RHS means right-hand side. The entire experimental isotherm can be fit using equation 6 to find a value for the desired parameter K$_{AX}$. This is, however, not necessary as shown in the following section.

X$_{0.5}$ is defined as the concentration of competing strand X at which θ=0.5, or exactly half of the acceptor/donor duplex, AD, has been disrupted. The value of X$_{0.5}$ can be interpolated from a plot of θ versus log[X]$_t$. When θ=0.5, a simple relation between the desired equilibrium constant K$_{AX}$, the measured value X$_{0.5}$, and the known values [D]$_t$ and K$_{AD}$ results in:

$$K_{AX} = \left(\frac{K_{AD}[D]_t}{2X_{0.5}}\right)$$ (Equation 7)

Application of the well known relation between ΔG° and K yields Equation 8:

$$\Delta G^o_{AX} = -RT \ln\left(\frac{K_{AD}[D]_t}{2X_{0.5}}\right)$$ (Equation 8)

The value of K$_{AD}$ will have been previously determined by independent methods such as differential scanning calorimetry and UV-absorbance melting. Alternate representations of equation 8 can be used to evaluate the free energy changes associated with the formation of the duplexes and the defects.

$$\Delta G^o_{AX} = \Delta G^o_{AD} - RT \ln\frac{D_t}{2X_{0.5}}$$ (Equation 9)

$$\Delta G^o_{AX} = -RT \ln K_{AD} - RT \ln\frac{D_t}{2X_{0.5}}$$ (Equation 10)

$$\Delta G^o_{AX} - \Delta G^o_{AD} = -RT \ln\frac{D_t}{2X_{0.5}}$$ (Equation 11)

Alternatively, the impact of a difference between two oligonucleotides (X$_1$ & X$_2$) on duplex stability, ΔΔG°, can be evaluated by titration (in separate experiments) of the two competitors against the same reference AD duplex at the same AD concentration (Equation 12).

$$\Delta\Delta G^o_{1-2} = \Delta G^o_1 - \Delta G^o_2 = -RT \ln\frac{X_{0.5,2}}{X_{0.5,1}}$$ (Equation 12)

In Equation 12, the value for $K_{AD}$ is cancelled. Therefore, one can evaluate the free energy impact of a single defect, or multiple defects, without thorough thermodynamic characterization of the AD duplex.

The assumption of $[X]_t \gg [AX]$ in equation 6 can be relaxed thereby leading to $$\theta = \frac{[A]_t(1-\theta)}{\frac{1+([X]_t-[AX])K_{AX}}{K_{AD}} + [D]_t(1-\theta)} \quad \text{(Equation 13)}$$

An unknown parameter [AX] must be evaluated as part of the calculation of $\theta$. This is accomplished by iteration over [AX] with the restriction that $[A]_t=[AX]+[AD]+[A]_f$. A second root finding problem is executed with the objective being finding a value of [AX] that satisfies the equation $$[A]_t - [AX] - \theta D_t - \frac{\theta}{K_{AD}(1-\theta)} = 0 \quad \text{(Equation 14)}$$

A second program is also shown in Example 5 that calculates theta ($[A]_t, [D]_t, [X]_t, K_{AD}, K_{AX}$) without the restriction that $[X]_t \gg [AX]$. While a useful reduction of equation 13 (similar to equations 7 and 8) cannot eliminate the need for iterative solution, values of $X_t$ at $\theta=0.5$ are readily calculated. Values of $X_t$ so calculated are compared to experimental values and $K_{AX}$ adjusted to produce the experimental value of $X_t$.

Comparison of isotherms calculated using equations 6 and 13 reveal that the error introduced by the assumption of negligible [AX] is small and only significant when $K_{AX} \sim K_{AD}$. For $K_{AX}/K_{AD}=1$, the error in free energy is about 0.4 kcal/mole; for $K_{AX}/K_{AD}=0.1$, 0.06 kcal/mole; and for $K_{AX}/K_{AD}=0.01$, 0.005 kcal/mole. Therefore, the assumption is in most cases reasonable. Those cases where it is not totally without adverse consequence, that is where $K_{AX} \sim K_{AD}$, are readily predictable, can be addressed easily by application of the full equation 13.

As is clear from the equations 7 and 8, the $K_{AX}$ and $\Delta G°_{AX}$ values that are measured are relative to the value of $K_{AD}$. As a practical matter, titration of X into the solution to a concentration of 1000 $[D]_t$ is convenient. An $X_{0.5}$ value of $1000[D]_t$ corresponds to a $\Delta\Delta G°$ value of about 4.5 kcal/mole ($\Delta\Delta G° = -$RTln (1/2000)). This is a rather large range and should accommodate most single base defects. The range can easily be extended by performing additional titrations using less stable AD duplexes. The stability of the AD duplexes can be modulated by inclusion of modified bases and/or mismatches. A series of AD duplexes can therefore be designed to cover essentially any range of $\Delta G°$ values, in intervals of 3 to 4 kcal/mole.

Analysis of the parallel titrations can be accomplished independently or collectively to determine the free energy values using the analysis described above.

Equation 6 can be rearranged and used to determine the concentration of a target sequence (X), when the values of $K_{AD}$ and $K_{AX}$ are known. In this example, a known volume and concentration of AD duplex is added to a known volume of an X containing solution. Alternatively, a known volume of X containing solution is added to a known volume of AD duplex containing solution of known concentration. Thus $[A]_t=[D]_t$ is known. The concentration of X, $[X]_t$, can be calculated from the relative change in fluorescence, $\theta$, using the formula $$[X]_t = \frac{K_{AD}}{K_{AX}}\{[A]_t(1-\theta)^2 - \theta\}/\theta \quad \text{(Equation 15)}$$

When the temperature is controlled during the annealing process of a titration, additional information can be obtained. The cooling process can be performed in steps so that values of $\theta$ are collected as a function of temperature. Data at each temperature are used to produce a family of titration curves. Each curve is analyzed independently and values for $K_{AX}$ are determined as a function of temperature. The van't Hoff equation, $$\Delta H° = -R(\partial \ln K/\partial(1/T)) \quad \text{(Equation 16)}$$

can be used to extract enthalpy ($\Delta H°$) data. The thermodynamic description, at a given temperature is completed by using $\Delta G° = -$RTlnK and $\Delta S° = (\Delta H° - \Delta G°)/T$.

Direct detection of formation of DNA duplexes by titration is extremely difficult because of the very low concentrations required for monitoring the equilibrium which are well below the operating range of traditional in-solution methods. A competition assay is usable over a wide range of instrumentally accessible concentrations. The method of the invention provides a more reliable measurement of nucleic acid complex stability over a very wide range of free energy values because the titration depends on the difference in stability between the initial donor/acceptor-containing duplex and the resulting competitor-containing duplex and not on their absolute free energy values. Therefore, the range of accessible free energy values can be tuned by choice of the initial donor/acceptor-containing duplex. Relative free energies are usually the desired experimental result and the method of the invention provides them directly. The lower detection limits of the fluorophores define the maximum difference in free energy that can be detected by the method. The use of fluorophore detection provides great sensitivity. The emission spectrum of the donor strand at 10 pM concentration has been visualized reliably using a photon-counting fluorometer. Further, it may be possible to push to even lower concentrations using higher quantum yield fluorophores, or newer constructs such as quantum dots.

Free energies calculated from the assay of the present invention have been demonstrated to be in agreement with those measured by extensive thermodynamic studies on individual duplexes. In these experiments, two titrations were performed at the same $D_t$ concentration, for two starting Watson-Crick FET duplexes, designated A•T and T•A, which differ only by the central base pair, out of the 13 pairs in the duplex. Competition on each duplex is from nearly the same single strand as present in the FET duplexes, except this single strand is unlabeled and has a tetrahydrofuranyl abasic "lesion" site (F) at the central base pair. Free energy values measured by this method compare quite favorably to those measured by extensive differential scanning calorimetry and UV absorbance melting experiments on these 13-mer duplexes containing a single tetrahydrofuranyl abasic site (F) in the central position. Specifically, using the FET assay, a value of $-14.5\pm0.1$ kcal/mole for formation of the F•T duplex was determined, compared with a value of $-15.1\pm0.6$ kcal/mole determined using DSC/UV melts. Similarly, using the FET assay a value of $-16.2\pm0.1$ kcal/mole was determined for formation of the F•A duplex compared with a value of $-16.0\pm0.4$ kcal/mole by DSC/UV melts. These results correspond to $\Delta\Delta G°$ values of $-1.7\pm0.2$ kcal/mole from FET and $-0.9\pm1.0$ kcal/mole from DSC/UV melting studies for substitution of an A residue for a T residue opposite the abasic site.

Because measurement depends on relative concentration, $[D]_t/[X]$, the method of the present invention can be used in any concentration regime. The appropriate concentration range is determined by the sensitivity of the detection system. Accordingly, $[D]_t$ is selected by one of skill to optimize the detection method. Due to practical limitations on the volume of titrant that can be added to the titrate, there are some practical limitations to the range of free energy values that can be covered by a single titration. However, this range is quite large. A convenient limit of the ratio $[D]_t/[X]_{0.5}$ is about 0.001. This corresponds to a factor of about 0.002 in association constant or 3.7 kcal/mol in free energy. Most defects affecting nucleic acid duplex stability, for example, for which reliable free energy data are available fall into this range.

However, since the measured free energy values depend on the ratio of $K_{AD}$ and $K_{AX}$ ($\Delta\Delta G°$), the appropriate choice of donor-acceptor duplex must be made for each titration. Because the complementarity of the component strand of the donor-acceptor reference duplex need be only sufficient to form the duplex and achieve moderate thermal stability, the assay may be tuned over a wide range of free energy values by introducing mismatches in the donor-acceptor reference duplex. By judicious choices of donor-acceptor duplexes, a series of three donor acceptor duplexes can cover a range of 11 kcal/mole in free energy. If titrations are done in parallel, use of such a family of duplexes relieves one of estimating the magnitude of $K_{AX}$ prior to performing the titration. In this embodiment of the method of the present invention, several donor/acceptor complexes are formed simultaneously. Each different donor or acceptor oligonucleotide differs slightly, while maintaining complementarity of the acceptor with the target (X) or employing an analogous system where X binds to the donor, to produce donor/acceptor pairs of differing stability. By appropriate selection of donor and acceptor dyes, it is possible to conduct multiple simultaneous titrations of X into a single solution. Spectroscopic discrimination of the various donor acceptor pairs provides multiple free energy determinations simultaneously. Judicious use of long and short Stokes shift donors can facilitate use of a common acceptor dye, thus streamlining assay design and/or performance.

The assay of the present invention can be adapted by immobilization to a variety of inert solid supports using technologies established for standard hybridization studies. In this embodiment, one of the strands of the reference duplex (either donor (D) or acceptor (A)) can be attached to the surface. The reference duplex can then be formed on that surface. Exposure to target will release the unattached strand, thereby producing the signal. Because concentration cannot be defined at a surface in the same way as in solution, comparison to a standard of known stability is required for quantitative results. However, immobilization facilitates the miniaturization and adoption of this assay to high throughput screening while providing the benefit of using FET and the competing equilibria to increase the sensitivity of measurement of differences in duplex stability. Immobilization may also allow for the construction of an array of donor/acceptor duplexes of differing stability. Such an array assures appropriate selection of the initial complex. Further, because ranges of the free energy differences measurable using the various initial complexes overlap, multiple complementary measurements can be made simultaneously.

Simultaneous titrations provide a number of additional advantages to this assay. With appropriately designed donor-acceptor reference complexes, the range of accessible free energy is multiplied by the number of duplexes titrated simultaneously. Thus, employing three simultaneous donor-acceptor duplex titrations means that the effective range of a single titration experiment becomes 9-12 kcal/mol, without expending any extra test strand. The enhanced range also means that a favorable outcome is likely in a single experiment, rather than having to explore various single donor acceptor duplexes to find one which has a free energy less than 3-4 kcal/mol higher than the test duplex. Second, this application provides a degree of multiplexing that reduces the time involved in each assay, and thereby enhances the ability to perform high throughput screening of nucleic acid variations. Thus, the simultaneous titrations are truly simultaneous rather than merely in parallel, meaning that all of the information is gathered using a single cuvette. The detailed theory supporting the simultaneous titration experiment is described below.

Single Acceptor/Multiple Donor or Multiple Acceptor/Single Donor Method

In principle, any number of donor-acceptor pairs could be included with selective excitation of the donors and a single acceptor. The limitation is imposed by the necessity of finding several donors with non-overlapping excitation spectra and sufficient Stokes shifts such that their emission spectra each overlap sufficiently the excitation spectrum of the acceptor. This method allows a series of AD complexes with varying $K_{AD}$ to be used simultaneously.

As an example, the case wherein there are 3 donors ($D_1$, $D_2$, $D_3$) and a single acceptor dye (A) is described; however, the number of donors is not limited to 3. The donors are discriminated by their distinct excitation wavelengths, $\lambda_1$, $\lambda_2$, $\lambda_3$, and would all have emission spectra sufficiently overlapping the excitation of the acceptor. The initial concentrations are $[D_1]_t=[D_2]_t=[D_3]_t=[A]_t/3$. The Donor and acceptor labeled strand can form any or all of the complexes $AD_1$, $AD_2$, $AD_3$, and AX. The equilibrium constants for the various complexes that form are enumerated below.

$$K_{AD_1} = \frac{[D_1 A]}{[D_1]_f [A]_f} = \frac{[D_1 A]}{([D_1]_t - [D_1 A])([A]_t - [D_1 A] - [D_2 A] - [D_3 A] - [AX])} \quad \text{(Equation 17A)}$$

$$K_{AD_2} = \frac{[D_2 A]}{[D_2]_f [A]_f} = \frac{[D_2 A]}{([D_2]_t - [D_2 A])([A]_t - [D_1 A] - [D_2 A] - [D_3 A] - [AX])} \quad \text{(Equation 17B)}$$

$$K_{AD_3} = \frac{[D_3 A]}{[D_3]_f [A]_f} = \frac{[D_3 A]}{([D_3]_t - [D_3 A])([A]_t - [D_1 A] - [D_2 A] - [D_3 A] - [AX])} \quad \text{(Equation 17C)}$$

$$K_{AX} = \frac{[AX]}{[X]_f [A]_f} = \frac{[AX]}{([X]_t - [AX])([A]_t - [D_1 A] - [D_2 A] - [D_3 A] - [AX])} \quad \text{(Equation 18)}$$

Analogously, three theta values, which differ by the excitation wavelength, can be defined.

$$\theta_n^{\lambda_1} = \frac{[AD_1]}{[D_1]_t} = \frac{I_{D_1}^{\lambda_1} - I_n^{\lambda_1}}{I_{D_1}^{\lambda_1} - I_{AD_1}^{\lambda_1}} \quad \text{(Equation 19A)}$$

$$\theta_n^{\lambda_2} = \frac{[AD_2]}{[D_2]_t} = \frac{I_{D_2}^{\lambda_2} - I_n^{\lambda_2}}{I_{D_2}^{\lambda_2} - I_{AD_2}^{\lambda_2}} \quad \text{(Equation 19B)}$$

$$\theta_n^{\lambda_3} = \frac{[AD_3]}{[D_3]_t} = \frac{I_{D_3}^{\lambda_3} - I_n^{\lambda_3}}{I_{D_3}^{\lambda_3} - I_{AD_3}^{\lambda_3}} \quad \text{(Equation 19C)}$$

and thus $$[AD_1] = \theta_n^{\lambda_1}[D_1]_t \quad \text{(Equation 20A)}$$

$$[AD_2] = \theta_n^{\lambda_2}[D_2]_t \quad \text{(Equation 20B)}$$

$$[AD_3] = \theta_n^{\lambda_3}[D_3]_t \quad \text{(Equation 20C)}$$

Combining equations 20 with equations 17 and 18 and knowledge of the three $K_{AD}$ values, allows for fitting for the value of $K_{AX}$. In principle, not all $K_{AD}$ values need be known. In this case, the increased number of unknowns complicates the analysis significantly.

An alternate model, in which $AD_1$, $AD_2$, and $AD_3$ are in equilibrium with $XD_1$, $XD_2$ and $XD_3$ can be derived analogously. Fitting here is more complex as the number of unknowns is larger-including $K_{AD_2}$ $K_{AD_1}$ $K_{AD_3}$ A treatment in which a single donor and multiple acceptors can be used when fluorescence energy transfer can be observed directly (when acceptor emission is observable) and the acceptor emission spectra do not overlap significantly. Derivation of appropriate equations for this case is straightforward and analogous to those derived for the above case.

Multiple Acceptor/Multiple Donor Methods

Several donor acceptor/complexes can be monitored in solution simultaneously. Each donor must have a unique excitation wavelength and each acceptor an absorbance spectrum corresponding to the emission of its donor. If emission of the acceptor is to be monitored, the emission spectra of the acceptors must be unique. Some correction for overlap can be made; however, such necessity complicates the data analysis. The number of donor acceptor pairs is, in principle, unlimited.

Multiple donor acceptor pairs are designated $A_1D_1$, $A_2D_2$, $A_3D_3$, etc. An example is provided using three AD pairs, but any number is possible. Equations accounting for the multiple simultaneous equilibria are described below.

$$K_{A_1D_1} = \frac{[A_1D_1]}{[D_1]_f[A_1]_f} \quad \text{(Equation 21A)}$$

$$= \frac{[A_1D_1]}{([D_1]_t - [A_1D_1] - [A_2D_1] - [A_3D_1])([A_1]_t - [A_1D_1] - [A_1D_2] - [A_1D_3] - [A_1X])}$$

$$K_{A_2D_2} = \frac{[A_2D_2]}{[D_2]_f[A_2]_f} \quad \text{(Equation 21B)}$$

$$= \frac{[A_2D_2]}{([D_2]_t - [A_1D_2] - [A_2D_2] - [A_3D_2])([A_2]_t - [A_2D_1] - [A_2D_2] - [A_2D_3] - [A_2X])}$$

$$K_{A_3D_3} = \frac{[A_3D_3]}{[D_3]_f[A_3]_f} \quad \text{(Equation 21C)}$$

$$= \frac{[A_3D_3]}{([D_3]_t - [A_1D_3] - [A_2D_3] - [A_3D_3])([A_3]_t - [A_3D_1] - [A_3D_2] - [A_3D_3] - [A_3X])}$$

$$K_{A_1X} = \frac{[A_1X]}{[X]_f[A_1]_f} \quad \text{(Equation 22)}$$

$$= \frac{[A_1X]}{([X]_t - [A_1X] - [A_2X] - [A_3X])([A_1]_t - [A_1D_1] - [A_1D_2] - [A_1D_3] - [A_1X])}$$

It is assumed that each X sequence will bind to $A_1$, $A_2$, and $A_3$ with equal affinity, since the three acceptor oligonucleotides have identical sequences. Therefore, $[XA_1] = [XA_2] = [XA_3]$ and $$K_{A_1X} = K_{A_2X} = K_{A_3X} \quad \text{(Equation 23)}$$

Similar reasoning leads to the assertion that $[D_1A_1] = [D_1A_2] = [D_1A_3]$ and so forth for the other donor sequences. Defining expressions for θ and substituting the following expressions for the equilibrium constants it is found that:

$$\theta_n^{\lambda_1} = \frac{[A_1D_1]}{[D_1]_t} = \frac{I_{D_1}^{\lambda_1} - I_n^{\lambda_1}}{I_{D_1}^{\lambda_1} - I_{A_1D_1}^{\lambda_1}} \quad \text{(Equation 24A)}$$

$$\theta_n^{\lambda_2} = \frac{[A_2D_2]}{[D_2]_t} = \frac{I_{D_2}^{\lambda_2} - I_n^{\lambda_2}}{I_{D_2}^{\lambda_2} - I_{A_2D_2}^{\lambda_2}} \quad \text{(Equation 24B)}$$

$$\theta_n^{\lambda_3} = \frac{[A_3D_3]}{[D_3]_t} = \frac{I_{D_3}^{\lambda_3} - I_n^{\lambda_3}}{I_{D_3}^{\lambda_3} - I_{A_3D_3}^{\lambda_3}} \quad \text{(Equation 24C)}$$

Therefore, $$\theta_n^{\lambda_1}[D_1]_t = [A_1D_1] = [A_2D_1] = [A_3D_1] \quad \text{(Equation 25A)}$$

$$\theta_n^{\lambda_2}[D_2]_t = [A_1D_2] = [A_2D_2] = [A_3D_2] \quad \text{(Equation 25B)}$$

$$\theta_n^{\lambda_3}[D_3]_t = [A_1D_3] = [A_2D_3] = [A_3D_3] \quad \text{(Equation 25C)}$$

Further assume that $[D_1]_t=[D_2]_t=[D_3]_t$, which is determined by the experimental setup.

$$K_{A_1D_1} = \frac{[A_1D_1]}{[D_1]_f[A_1]_f} \quad \text{(Equation 26A)}$$

$$= \frac{\theta^{\lambda_1}}{(1-3\theta^{\lambda_1})([A_1]_t(\theta^{\lambda_1}+\theta^{\lambda_2}+\theta^{\lambda_3})[D_1]_t - [A_1X])}$$

$$K_{A_2D_2} = \frac{[A_2D_2]}{[D_2]_f[A_2]_f} \quad \text{(Equation 26B)}$$

$$= \frac{\theta^{\lambda_2}}{(1-3\theta^{\lambda_2})([A_2]_t(\theta^{\lambda_1}+\theta^{\lambda_2}+\theta^{\lambda_3})[D_2]_t - [A_2X])}$$

$$K_{A_3D_3} = \frac{[A_3D_3]}{[D_3]_f[A_3]_f} \quad \text{(Equation 26C)}$$

$$= \frac{\theta^{\lambda_3}}{(1-3\theta^{\lambda_3})([A_3]_t(\theta^{\lambda_1}+\theta^{\lambda_2}+\theta^{\lambda_3})[D_3]_t - [A_3X])}$$

$$K_{A_1X} = \frac{[A_1X]}{[X]_f[A_1]_f} \quad \text{(Equation 27)}$$

$$= \frac{[A_1X]}{([X]_t - 3[A_1X])([A_1]_t(\theta^{\lambda_1}+\theta^{\lambda_2}+\theta^{\lambda_3})[D_1]_t - [A_1X])}$$

Equations for $K_{A_2X}$ and $K_{A_3X}$ assume similar forms and as noted above are assumed equal to $K_{A_1X}$ This system of equations (Equations 26 & 27) must be solved by iterative methods to find a value of $K_{AX}$ which satisfies, at each $X_t$, the constraints imposed by the known concentrations of the AD complexes derived from the measured $\theta$ values.

A fundamentally different strategy for simultaneous monitoring of multiple donor/acceptor pairs is to use the dyes as acceptor and donor, but on different duplexes. Again, discrimination is made optically. Here, an example is provided using three donor/acceptor complexes, but the method is not limited in the number of complexes that can be employed.

The nomenclature is altered slightly from that used above. Here, each fluorescent dye is designated as D, with superscript A indicating that dye D is acting as an acceptor and superscript D indicating that dye D is acting as a donor. Dyes are attached to oligonucleotides such that three FET-capable duplexes can form: $D^A_2D^D_1$, $D^A_3D^D_2$, and $D^A_4D^D_3$. Dye $D_1$ acts only as a donor and $D_4$ only as an acceptor; however, dyes $D_2$ and $D_3$ act as acceptor and donor, but on different duplexes. Again, the oligonucleotides are designed so that $D^A_2D^D_1$, $D^A_3D^D_2$, and $D^A_4D^D_3$ vary in stability systematically and so that the X strand can form duplexes with the acceptor bearing strands, namely $D^A_2X$, $D^A_3X$ and $D^A_4X$.

As in the cases described above, equilibrium constants can be derived relating the concentrations of the various solution components.

$$K_{D^A_1D^D_1} = \frac{[D^A_2D^D_1]}{[D^D_1]_f[D^A_2]_f} \quad \text{(Equation 28A)}$$

$$= \frac{[D^A_2D^D_1]}{([D^D_1]_t - [D^A_2D^D_1] - [D^A_3D^D_1] - [D^A_4D^D_1])([D^A_2]_t - [D^A_2D^D_1] - [D^A_2D^D_2] - [D^A_2D^D_3] - [D^A_2X])}$$

$$K_{D^A_1D^D_2} = \frac{[D^A_3D^D_2]}{[D^D_2]_f[D^A_3]_f} \quad \text{(Equation 28B)}$$

$$= \frac{[D^A_3D^D_2]}{([D^D_2]_t - [D^A_2D^D_2] - [D^A_3D^D_2] - [D^A_4D^D_2])([D^A_3]_t - [D^A_3D^D_1] - [D^A_3D^D_2] - [D^A_3D^D_3] - [D^A_3X])}$$

$$K_{D^A_1D^D_3} = \frac{[D^A_4D^D_3]}{[D^D_3]_f[D^A_4]_f} \quad \text{(Equation 28C)}$$

$$= \frac{[D^A_4D^D_3]}{([D^D_3]_t - [D^A_2D^D_3] - [D^A_3D^D_3] - [D^A_4D^D_3])([D^A_4]_t - [D^A_4D^D_1] - [D^A_4D^D_2] - [D^A_4D^D_3] - [D^A_4X])}$$

Because the acceptor strands are not identical (the dyes differ although the oligonucleotides to which they are attached are identical), there are three additional equilibrium constants to define.

$$K_{D^A_2X} = \frac{[D^A_2X]}{[D^A_2]_f[X]_f} \quad \text{(Equation 29A)}$$

$$= \frac{[D^A_2X]}{([D^A_2]_t - [D^A_2D^D_1] - [D^A_2D^D_2] - [D^A_2D^D_3] - [D^A_2X])([X]_t - [D^A_2X] - [D^A_3X] - [D^A_4X])}$$

$$K_{D^A_3X} = \frac{[D^A_3X]}{[D^A_3]_f[X]_f} \quad \text{(Equation 29B)}$$

$$= \frac{[D^A_3X]}{([D^A_3]_t - [D^A_3D^D_1] - [D^A_3D^D_2] - [D^A_3D^D_3] - [D^A_3X])([X]_t - [D^A_2X] - [D^A_3X] - [D^A_4X])}$$

$$K_{D^A_4X} = \frac{[D^A_4X]}{[D^A_4]_f[X]_f} \quad \text{(Equation 29C)}$$

$$= \frac{[D^A_4X]}{([D^A_4]_t - [D^A_4D^D_1] - [D^A_4D^D_2] - [D^A_4D^D_3] - [D^A_4X])([X]_t - [D^A_2X] - [D^A_3X] - [D^A_4X])}$$

If the dyes do not perturb the equilibria significantly, it is reasonable to assume that $K_{D^A_2X}=K_{D^A_3X}=K_{D^A_4X}$. The assump tion that the acceptor dyes are equally perturbing or non-perturbing is reasonable and testable.

$$\theta_n^{\lambda_1} = \frac{[D_2^A D_1^D]}{[D_1^D]_t} \quad \text{(Equation 30A)}$$

$$= \frac{I_{D_1^D}^{\lambda_1} - I_n^{\lambda_1}}{I_{D_1^D}^{\lambda_1} - I_{D_2^A D_1^D}^{\lambda_1}}$$

$$\theta_n^{\lambda_2} = \frac{[D_3^A D_2^D]}{[D_2^D]_t} \quad \text{(Equation 30B)}$$

$$= \frac{\left(I_{D_2^D}^{\lambda_2} + I_{D_3^A}^{\lambda_2}\right) - \left(I_n^{\lambda_2} + I_{D_2^A}^{\lambda_2}\right)}{\left(I_{D_2^D}^{\lambda_2} + I_{D_3^A}^{\lambda_2}\right) - \left(I_{D_3^A D_2^D}^{\lambda_2} + I_{D_2^A}^{\lambda_2}\right)}$$

$$= \frac{I_{D_2^D}^{\lambda_2} - I_n^{\lambda_2}}{I_{D_2^D}^{\lambda_2} - I_{D_3^A D_2^D}^{\lambda_2}}$$

$$\theta_n^{\lambda_3} = \frac{[D_4^A D_3^D]}{[D_3^D]_t} \quad \text{(Equation 30C)}$$

$$= \frac{\left(I_{D_3^D}^{\lambda_3} + I_{D_3^A}^{\lambda_3}\right) - \left(I_n^{\lambda_3} + I_{D_3^A}^{\lambda_3}\right)}{\left(I_{D_3^D}^{\lambda_3} + I_{D_3^A}^{\lambda_3}\right) - \left(I_{D_4^A D_3^D}^{\lambda_3} + I_{D_3^A}^{\lambda_3}\right)}$$

$$= \frac{I_{D_3^D}^{\lambda_3} - I_n^{\lambda_3}}{I_{D_3^D}^{\lambda_3} - I_{D_4^A D_3^D}^{\lambda_3}}$$

Note that in the expressions for $\theta_n^{\lambda_2}$ and $\theta_n^{\lambda_3}$ the measured quantities (shown in parentheses) contain contributions from the fluorescence of the acceptor of the previous (as in the assigned index) donor acceptor pair. This is assumed to be independent of the formation of the complex. This assumption is testable. Should it not be valid, appropriate corrections can be applied.

As in the above analyses, the concentrations of the donor/acceptor complexes can be determined by measurement of the $\theta$ values and knowledge of the total concentrations of the donor strands.

$$[D_2^A D_1^D] = \theta_n^{\lambda_1}[D_1^D]_t \quad \text{(Equation 31A)}$$

$$[D_3^A D_2^D] = \theta_n^{\lambda_2}[D_2^D]_t \quad \text{(Equation 31B)}$$

$$[D_4^A D_3^D] = \theta_n^{\lambda_3}[D_3^D]_t \quad \text{(Equation 31C)}$$

Again substituting values for the $\theta$ terms and assuming that $[D_1^D]_t = [D_2^D]_t = [D_3^D]_t$, which is determined by the experimental setup, a system of equations is presented that can be solved as a function of $[X]_t$ to find values for $K_{D_2^A X} = K_{D_3^A X} = K_{D_4^A X}$ $$K_{D_2^A D_1^D} = \frac{[D_2^A D_1^D]}{[D_1^D]_f [D_2^A]_f} \quad \text{(Equation 32A)}$$

$$= \frac{\theta_n^{\lambda_1}}{(1 - 3\theta_n^{\lambda_1})([D_2^A]_t - (\theta_n^{\lambda_1} + \theta_n^{\lambda_2} + \theta_n^{\lambda_3})[D_1^D]_t - [D_2^A X])}$$

$$K_{D_3^A D_2^D} = \frac{[D_3^A D_2^D]}{[D_2^D]_f [D_3^A]_f} \quad \text{(Equation 32B)}$$

$$= \frac{\theta_n^{\lambda_2}}{(1 - 3\theta_n^{\lambda_2})([D_3^A]_t - (\theta_n^{\lambda_1} + \theta_n^{\lambda_2} + \theta_n^{\lambda_3})[D_2^D]_t - [D_3^A X])}$$

$$K_{D_4^A D_3^D} = \frac{[D_4^A D_3^D]}{[D_3^D]_f [D_4^A]_f} \quad \text{(Equation 32C)}$$

$$= \frac{\theta_n^{\lambda_3}}{(1 - 3\theta_n^{\lambda_3})([D_4^A]_t - (\theta_n^{\lambda_1} + \theta_n^{\lambda_2} + \theta_n^{\lambda_3})[D_3^D]_t - [D_4^A X])}$$

$$K_{D_2^A X} = \frac{[D_2^A X]}{[D_2^A]_f [X]_f} \quad \text{(Equation 33)}$$

$$= \frac{[D_2^A X]}{([D_2^A]_t - (\theta_n^{\lambda_1} + \theta_n^{\lambda_2} + \theta_n^{\lambda_3})[D_2^A]_t - [D_2^A X])([X]_t - 3[D_2^A X])}$$

Expressions for $K_{D_3^A X}$ and $K_{D_4^A X}$ are derived similarly and, as described above, their values are assumed to be identical to $K_{D_2^A X}$ The advantage of this method of multiple simultaneous titration, where some of the dyes act as both donor and acceptor (although on different oligonucleotides), over the method described above, in which all donors and acceptors are unique, is that the probability of identification of a set of fluorescent dyes with the necessary photophysical properties is enhanced.

While there are restrictions on the properties of a set of dyes usable in simultaneous titrations, there are likely to be many sets of usable dyes. One such set of dyes is described in the table below. Each of them is available from Molecular Probes, Inc. of Eugene, Oreg.

| Donor | Acceptor | Fluorescent Dye |
|---|---|---|
| $D_1^D$ | — | Alexa 350 |
| $D_2^D$ | $D_2^A$ | Alexa 430 |
| $D_3^D$ | $D_3^A$ | Alexa 488 |
| — | $D_4^A$ | Alexa 594 |

When one of the reference duplex strands is attached to a surface, only the other strand need be labeled. In this embodiment, the measurement is not FET, but rather fluorescence. A washing step must be included in this embodiment to remove released label. However, the washing step may disturb the equilibria rendering this embodiment of the assay more qualitative than quantitative.

Alternative embodiments could avoid some of the complications caused by washing. Detection of the solid-phase attached signal could be made with confocal microscopy, taking advantage of the diffusion of dissociated fluorophore-bearing strand which should reduce the local concentration, and consequently reduce the detected fluorescence accordingly. Alternatively, excitation by evanescent wave guide through a glass solid support should have the ability to excite primarily bound fluorophores, allowing bound versus free discrimination.

Multiple measurements can be conducted simultaneously on a surface. A series of different strands can be attached to a surface so as to identify a particular oligonucleotide with its location on the surface. This kind of spatial distribution of different oligonucleotides, often referred to as oligonucleotide arrays, is well known. The fluorophore can be attached post-synthetically or as a phosphoramidite; either method is compatible with methods for producing an oligonucleotide array on a surface. A single oligonucleotide with sufficient complementarity to form reference duplexes with each of the immobilized strands can be used to form a series of reference duplexes. The surface is then exposed to a single target that simultaneously equilibrates with all of the reference duplexes. A series of standards can be routinely incorporated into this assay.

The method of the present invention is of particular use in single nucleotide polymorphism (SNP) screening. The theory behind the application of this FET assay to SNP screening is based upon two segments of DNA, the first being the "major allele" base (the common base or so-called "wild type" base), and the second being the "minor allele" (the less common base, a variant, or a mutation) that, for example, may be a marker for disease or disease predisposition. Standardized methods abound for amplifying a small genetic sample (e.g. from a few microliters of blood). For the current method, this amplified duplex should be reduced to a single strand, by one of various chemical or biochemical methods, known to those skilled in the art, which would become the unlabeled competitor (X) strand in our FET assay. When amplification of the target is performed, the quantity of the target can be determined by use of labeled primers. The labeled primers are either fluorescently labeled, so as not to interfere with the subsequent FET measurement, or labeled by any of the many well known methods for labeling amplification products. Alternatively, the singly labeled fluorescent primer could serve as the donor of a FET pair, such that the usual AX as described is positive for FET, and the starting "D" A pair is now silent (where "D" is now actually an unlabeled strand). In this case, the FET signal increases with increasing AX formation, and the mathematical analysis is adjusted accordingly.

Since SNP screening is merely a detection of alternative SNP alleles, almost in a quantized analysis, and not quantitation of energetic impact per se, FET-based SNP screening does not even require a full titration of target (X) into the donor-acceptor duplex. Merely adding a fixed excess amount of the X strand is sufficient, in effect making a two-point titration wherein the fluorescence is measured before and after X addition. The amount of X strand needed should be in the range of 10- to 100-fold excess over donor (D). In these experiments, when the sequences of X and D match, X will efficiently displace D from the donor acceptor duplex, causing an efficient, and probably complete, reduction in θ. When X and D do not match, θ will remain high. In theory, either experiment would be sufficient to prove the presence or absence of wild-type sequence. However, it is generally preferable to guarantee that a positive and negative signal will be achieved in clinical assays, so it would be preferable to run two experiments in parallel, monitoring donor-acceptor duplexes of major and minor SNP alleles, one of which should have high θ and low θ for homozygous targets. A heterozygous sample would score as an efficient competitor for both donor-acceptor duplexes.

The assay is further applicable to situations where there may be multiple SNP sites within a single gene, with each variation occurring at low frequency. In this embodiment, a much longer sequence can be screened similarly, still in a single experiment. In such a case, the donor-acceptor duplex has the wild-type sequence of the full length of the region of interest. The amplified target strand, X, is judged, from a single 10- to 100-fold addition, to either compete or not for the donor-acceptor duplex. If FET is reduced, and X is a good competitor, then further screening could be done using additional assays more specific in nature to the sequences in question. Even if another specific screening method is preferred, the global nature of the FET assay is useful as a first screen, eliminating the cost and expense of screening by other more detailed methods for every single patient being tested. If, among all SNPs identified within a gene, the frequency runs as high as 20% for having any one minor allele, the single screen using a very long sequence would still eliminate the need for extensive testing on 80% of the samples. This would represent a large savings in material, and would greatly improve the throughput of testing facilities.

The SNP assay is not significantly limited by the length of the strands (e.g. number of bases long) that are being screened. The actual length limitation is a theoretical barrier attributable to a kinetic situation whereby very long uniquely complementary sequences may not ever form a complete duplex. This limitation is similar to the fact that long sequences such as complete bacterial genomes cannot be completely reannealed after thermal disruption. The barrier for this assay is estimated to be in the range of several hundreds of bases, such that sequences of interest in the range of up to 100 bases can be easily accommodated. Clearly, longer sequences, however, are considered within the scope of this assay.

The relevance of a strand length of about 100 bases, however, is that regions bearing even one SNP may be assessed by a single assay, using this method. As SNP identity becomes linked to disease predisposition in humans, such screening becomes an extremely valuable technique for rapid diagnosis of individual patients, both for diagnosis of ailment, infection, drug sensitivity, drug resistance, etc., and early detection of conditions that can lead to timely application of preventative treatments. Regions of genes already identified as having relevant SNPs are generally in the range of 100 bases or less, meaning that the theoretical length limitation will not become a factor for the majority of applications.

The key feature of this method that eliminates length of the oligonucleotides as a limitation, unlike in other assays under commercial development, is that this method depends on competition between two different equilibria characterized by two different equilibrium constants. Thus the actual measurement is the ratio of the two equilibrium constants, and thus the difference in free energies for formation of these alternative duplexes. The difference in free energy caused by a defect, such as a single base pair mismatch (i.e. not a canonical Watson-Crick pairing), is the same whether the defect is within a very long duplex or a short one, so long as the bulk of the duplex generally remains stable. Thus, the magnitude of $\Delta G°$ is not a consideration, since the fluorescence assay measures the difference in two $\Delta G°$ values ($\Delta\Delta G°$) directly. Mismatches of the four canonical bases will generally exhibit $\Delta\Delta G°$ values of about 1 or 2 kcal/mol, but this 1 to 2 kcal/mol is the actual magnitude of the measurement itself. Thus, whether the absolute values are 20 kcal/mol of duplex, as in a 10-15 base pair oligonucleotide, or 600 kcal/mol of duplex, in a target several hundred bases long, the assay is silent to these magnitudes, because it is reporting $\Delta\Delta G°$ directly.

Fluorescently labeled strands used in the present invention may be provided in a kit form. A researcher interested in adapting their test DNA lesion could do so simply by synthesizing a small amount of test DNA within a sequence predefined by the kit DNA. A kit would include at least one FET-labeled starting duplex and the appropriate buffer along with instruction material for performing the experiment and analyzing the data. The kit may also include a standardized competitor strand to ensure reproducibility and to facilitate comparisons over time. As an example, the strands of a kit could be designed with specific targets in mind. A specific kit could be designed, for example, to screen for a single mutation in a gene. Alternatively, nucleic acid strands can be provided that are labeled with specific binding pairs.

The following nonlimiting examples are provided to further illustrate the present invention.

EXAMPLE 1

Purification and Dye-Labeling of 5'-Amino-Linker Oligonucleotides

Standard phosphoramidite DNA synthesis with an amino-linker phosphoramidite as the last (5') residue is performed. The intact synthesis column is dried under vacuum. The column is then cracked open and the glass support beads are transferred to a screw top plastic bottle. Aqueous $NH_4OH$ (1 ml) from the freezer is added to each tube and the DNA is deprotected for three days at room temperature for standard amidites. Tubes are then cooled in the freezer and the $NH_4OH$ is pipetted off. The supports are then washed with 2×200 µl water or a mixture of $EtOH:CH_3CN:H_2O$ (3:1:1); the samples and washes are combined; and then dried in a Speed-Vac. The dried samples are then dissolved in $H_2O$ at low temperature (<40° C.) and floating non-soluble materials are removed. At this step, the sample may be purified by reverse phase, using high performance liquid chromatography (HPLC) and a PRP-column, equilibrated with 50 mM ammonium bicarbonate. Elution is performed by a linear (5-50%) gradient of acetonitrile in 50 mM $NH_4HCO_3$. Following freeze-drying, the fractions containing the purified tritylated N-modified oligonucleotide are heated to 95° C. for 5 minutes to remove the MMT-(trityl) group and subjected to ethanol precipitation in the presence of sodium ions, as follows: the volume is adjusted to 300 to 400 µl water; NaCl (100 µl, 2M) or sodium buffer is then added along with 950 µl of EtOH; samples are then placed in the freezer for at least 30 minutes, preferably one hour. Following freezing, the sample is centrifuged for 12 minutes at 14,000 rpm. The resulting pellet is dried to remove any residual ethanol. Trityl is then removed by addition of 200 µl of 80% acetic acid for one hour at room temperature and evaporating the liquid in a Speed-Vac for 2 to 3 hours until a glassy residue is observed. This step is critical to ensure elimination of any residual free amines that might interfere with the labeling reaction. For the unlabeled oligonucleotides, the trityl group is removed by addition of 80% acetic acid and incubation for one hour at room temperature, followed by freeze drying. Both the purity of the final product and the success of detritylation are monitored by analytical reverse phase HPLC. If required, additional purification of the detritylated oligonucleotide is performed by reverse phase HPLC. The purified DNA is subjected to ethanol precipitation/Na+ exchange to rid the sample of any excess reactive amines from the HPLC buffer and labeled as follows: DNA (30-40 OD-260) is dissolved in 270 µl of $H_2O$ in an O-ring tube. $NaHCO_3$ (30 µl, 1 M) at pH 8.3 is then added. One mg of succinyl ester form of the dye is then added for each 20 OD of DNA. This can be weighed as a dry reagent into a glass vial, dissolved in 80 µl/mg of fresh DMSO, and added into the plastic tube of DNA solution. The glass vial is then rinsed with 20 µl of additional DMSO and added to the plastic tube. Alternatively, a 100 µl aliquot of dye is added. The dye and DNA are then allowed to react at 37° C. or higher at least overnight.

The DNA is then isolated from any unreacted dye with a PD-10 Sephadex G-25 column (Pharmacia). The column is equilibrated by rinsing with at least 25 ml of $H_2O$. The DNA sample is diluted with $H_2O$ to a final volume of 1000 µl and loaded onto the column. The DNA is then washed using 1.6 ml $H_2O$. DNA is eluted in 600 µl fractions with $H_2O$. Generally six fractions are sufficient.

The fractions are dried to at least ½ the volume and adjusted to 300 µl total volume with $H_2O$. Each fraction is then independently subjected to ethanol precipitation. Generally only the first three fractions will have appreciable DNA. The free dye stays mostly dissolved in the ethanol.

The DNA containing precipitates are combined and the labeled DNA purified using ion exchange HPLC (Mono-Q column) with Buffer A being 50 mM Tris HCl with 15% acetonitrile and Buffer B being Buffer A with 1 M NaCl. The gradient profile can be tailored but in general increases from 0 to 80% buffer B over 25-35 minutes. Monitoring absorbance at both 260 nm and the absorbance maximum of the attached fluorophore can help to define the labeled and unlabeled DNA peaks.

The labeled DNA is further purified by HPLC using an ion exchange column (e.g. Mono Q, Pharmacia) equilibrated with 50 mM Tris HCl and 15% Acetonitrile (Buffer A) and a linear gradient (0-100%) of Buffer B (i.e., Buffer A containing 1 M NaCl). Absorbances at 260 nm and the wavelength corresponding to the maximum absorbance of the fluorophore are use to monitor and define labeled and unlabeled pools of oligonucleotides.

Alternatively, a desalting column can be used in place of the ethanol precipitation steps.

5'-labeled oligonucleotides forming duplexes have been compared with the parent unlabeled duplexes, revealing no alterations in their thermodynamic stability in the presence of the probes. Moreover, the ability to form Watson-Crick duplexes in a stoichiometric ratio has been further confirmed by HPLC analysis of the annealed mixtures, in comparison to the free oligonucleotide strands. Additional evidence reveals that both labeled and unlabeled oligonucleotides may be recovered upon completion of a FET assay by repurification, with no indication of adulteration. Time-dependent studies of the integrity of the labeled oligonucleotides reveal no sign of aggregation or degradation within 1 year from sample preparation. The labeled oligonucleotides may be stored as stock solutions in water and working buffer at or below −20° C. for at least six months. Preferably, the samples should be stored as a lyophilized powder, for periods exceeding six months.

EXAMPLE 2

Determination of Labeled DNA Concentration

Determination of the concentration of the labeled DNA strands in stock solutions has been performed using an average extinction coefficient of $1.1 \times 10^5$ $M^{-1}cm^{-1}$ at 25° C. The intrinsic DNA absorbance at 260 nm has been demonstrated to not be significantly altered by the presence of the conjugated dye.

EXAMPLE 3

Formation of the FET Duplex

A working stock solution of each of the labeled DNA of complementary sequence in the range of 2 to 3 micromole DNA strand is prepared. Fluorescence detection is performed as follows: after each aliquot (of any titrant) the cuvette is heated to about 90° C., using an external heat block, and cooled to 25° C. via the intrinsic cooling of the jacketed cuvette holder in the fluorometer. The cuvette must be tightly stoppered to minimize evaporation during heating. Wavelengths must be tailored for the dyes used. For example, for the fluorophore pair Oregon Green 514 and Rhodamine-Red-X, the emission spectrum is collected over 510-650 nm with excitation at 508 nm, with scanning at 100 nm per minute. The time drive is set to collect, using the kinetics mode, 30 or 60 seconds (at 0.1 second per reading) using 508 nm excitation and 528 nm emission. These data points are then averaged, resulting in a precise relative fluorescence intensity for each reading, and an associated standard deviation for that averaged value. The fluorescence of the buffer alone is read to establish a blank for the instrument response.

The fluorescence of the "free" donor strand is then determined. A sample of 10 nM donor strand is prepared in 250 µl total volume of buffer and fluorescence is measured. An aliquot of the acceptor strand from the working stock sufficient to achieve a final concentration of 100 nM is then added to form the FET duplex and the fluorescence is determined.

EXAMPLE 4

Titration of the Competing Strand

A working stock of the competing strand is prepared at a concentration appropriate to the expected ability/inability to compete for duplex formation with the formed donor/acceptor pair. In general, the concentration is one order of magnitude higher than the donor and acceptor working stocks for each 1 kcal/mol of free energy difference (ΔΔG) expected for the competing strand. In the event the free energy differences are completely unknown, a number of concentrations can be prepared, covering a wide range of concentrations, i.e., 2 µM, 20 µM, 200 µM, etc. solutions in buffer. Titration is started with the most dilute solution and more concentrated solutions are used as necessary.

For the first aliquot, the competing strand is added to a final concentration of about ½ of the concentration of the donor/acceptor concentration. The fluorescence is then determined. If there is a significant change in the fluorescence, titration is continued with the working stock. If there is no change, titration is continued with a higher working stock concentration. Additional aliquots are added and the fluorescence determined until the fluorescence intensity recovers to at least ½ of the intensity measured for the free donor strand.

EXAMPLE 5

Automation of Competitive Titration Experiment

The FET data acquisition protocol was automated on an AVIV Model ATF-105 Automatic Titrating Fluorescence Spectrophotometer. The customized software developed for the FET assay on this particular instrument improved the overall accuracy, precision, and data throughput compared to conventional manual titration experiments. There are several key features of the automated FET assay including programmed titration of acceptor and competitor or target strands and the ability to conduct successive heating/cooling cycles of the sample solution in the cuvette. Selection of the upper temperature limit is dictated by two important considerations, namely that the parent and test duplexes are dissociated into single strands and the covalently attached fluorophores are stable at the desired upper temperature. Extensive control studies conducted on the stability of the Oregon Green 514 (OG) and Rhodamine-Red-X (RdRX) labeled strands indicate that these fluorophores retain their integrity during successive heating/cooling cycles over the temperature range of 0-75°. The superimposition of UV melting/cooling curves reveled that the fluorescently labeled strands in the parent duplex are not labile below 75° C. The overall reproducibility is compromised when heating the identical duplex to temperatures above 75° C., as noted in the family of non-superimposable UV melting/cooling curves. It is incumbent upon the analyst to judiciously evaluate and select the practical upper temperature limit for a particular duplex and set of fluorophores.

A typical experiment is initiated by placing a cuvette containing a 100 nM solution of the Oregon Green 514 labeled donor strand in the sample compartment, heating the cuvette to 75° C., maintaining the temperature at 75° C. for three minutes, and cooling the sample to 20° C. over an equilibration period of five minutes. During the cooling cycle, the instrument is operated in the kinetic mode and the fluorescence emission intensity is recorded at 521 nm (i.e. excitation wavelength=508 nm) at five second intervals. After the fluorescence intensity plateaus indicating that equilibrium is achieved, a reference spectrum of the donor strand is recorded over the wavelength range of 510-650 nm. Activation of the first syringe drive dispenses fixed microliter aliquots of the Rhodamine-Red-X labeled acceptor strand in the sample cuvette to form the FET-active donor-acceptor reference duplex. Upon addition of each aliquot of acceptor, the sample is subjected to a heating/cooling cycle identical to that above to ensure that the duplex anneals properly. The donor strand (D) d (GCGTACACATGCG)-OG (SEQ ID NO: 1) is titrated with its complementary acceptor strand (A) d (CGCATGT-GTACGC)-RdRX (SEQ ID NO: 2) to form the FET-active reference donor-acceptor duplex. The diluted corrected fluorescence intensities are cast in the form of a Job Plot to confirm that the stoichiometry of the single strands in the reference duplex is 1:1 (i.e. mole fraction=0.5). Although the forward titration demonstrates that the single strands associate to form a competent duplex, the experimental protocol may be simplified by loading the pre-formed reference duplex into the cuvette prior to conducting the automated competition experiment. Elimination of the forward titration increases the sample throughput by reducing overall experimental time in the FET assay by approximately 50 percent.

Having formed the FET active reference duplex in the initial part of the experiment, the second syringe drive is activated to dispense fixed aliquots of the unlabeled competing strand (X) d (CGCATGFGTACGC) (SEQ ID NO: 3). The sample solution containing the three strands is subjected to heating/cooling cycles after each addition in the titration experiment to facilitate annealing of the donor-acceptor and acceptor-target (AX) duplexes. A sufficient excess of the target strand X (in this case approximately 100 fold) is titrated into the cuvette to ensure that at least half of the acceptor has been displaced from the reference duplex. The dilution corrected relative fluorescence (θ) is plotted as a function of the concentrations of acceptor (A) and target (X) strands. The concentration of competing strand ($X_{0.5}$) at which exactly half of the acceptor/donor duplex (AD) is disrupted, that is θ=0.5, is interpolated from this plot. Substituting the value for $X_{0.5}$ into the simplified relation:

$$K_{AX} = (K_{AD} \cdot D_t / 2 \cdot X_{0.5})$$

yields a value for the acceptor/target association constant ($K_{AX}$). Application of the thermodynamic relation between $\Delta G°$ and $K_{AX}$ facilitates calculation of the free energy:

$$\Delta G° = -R \cdot T \cdot \ln K_{AX}$$

In this example, values of $X_{0.5}=1.1\times10^{-5}$ for d(CGCATGF-GTACGC) (SEQ ID NO: 3) and $D_t=4.22\times10^{-8}$ for d(GCG-TACACATGCG)-OG (SEQ ID NO: 1), coupled with a $K_{AD}=9.0\times10^{14}$ determined independently for the reference duplex, results in a $K_{AX}=1.7\times10^{12}$ for the formation of the AX duplex. Substitution into the relevant relation yields a value of $\Delta G°=16.4$ kcal/mol for the AX duplex that compares favorably with the value determined previously (i.e. $\Delta G°=16.0$ kcal/mol) employing a combination of calorimetric and spectroscopic technique.

EXAMPLE 6

Equation Programs

Equation 6 Program
```
'declare globals'
Dim At, Dt, Xt, Kad, Kax As Double
Function theta (zl, z2, z3, z4, z5) As Double
At =zl
Dt=z2
Kad=z3
Kax=z4
Xt=z5
theta=ModRegFal (0#, 1#)
End Function
Private Function func1 (A) As Double
func1=At*(1-A)/((1+Xt*Kax)/Kad+Dt*(1-A))-A
End Function
Private Function ModRegFal (Xl, X2 As Double) As Double
'Modified Regula Falsi'
'(adapted from Conte & de Boor, 1980)'
'Finds root of function func1, if bracketed'
Const xtol=0.000000000001
Const ftol=0.000000000000001
Const ntol=100
Dim SignF1, n, PrvsF3 As Integer
Dim F1, F2, F3, X3 As Double
F1=func1 (XL)
F2=func1 (X2)
'test whether root is bracketed'
If Sgn (F1)*F2>0 Then
    Debug.Print "X1= ", X1, "X2= ", X2
    Debug.Print "func1 (X1)=", F1, "func1 (X2)=", F2
    End
End If
X3=X1
F3=F1
'BEGIN ITERATION'
For n=1 To ntol
    'TEST FOR CONVERGENCE'
    'Is interval small enough?'
    If Abs(X1-X2)<=xtol Then
        ModRegFal=X3
        Exit Function
    End If
    'Is F3 small enough?'
    If Abs (F3)<=ftol Then
        ModRegFal=X3
        Exit Function
    End If
    'GET NEW GUESS BY LINEAR INTERPOLATION'
    X3=(F1*X2-F2*X1)/(F1-F2)
    PrvsF3=Sgn(F3)
    F3=func1 (X3)
    'CHANGE TO NEW INTERVAL'
    If Sgn (F1)*F3>=0 Then
        X1=X3
        F1=F3
        If F3*PrvsF3>=0 Then F2=F2/2#
    Else
        X2=X3
        F2=F3
        If F3*PrvsF3>=0 Then F1=F1/2#
    End If
Next n
'END ITERATION'
Debug.Print "X1= ", X1, "X2= ", X2, "X3= ", X3
Debug.Print "func1 (X1)= ", F1, "func1 (X2)= ", F2, "func1 (X3)= ", F3
Debug.Print ntol, "iterations without convergence"
End Function
```

Equation 13 Program
```
'declare globals'
Dim At As Double, Dt As Double, Xt As Double
Dim XA As Double, Kad As Double, Kax As Double
Dim AX As Double
Function theta (zl#, Z2#, Z3#, Z4#, Z5#) AS Double
At =zl
Dt=z2
Kad=z3
Kax=z4
Xt=z5
dummy=ModRegFal2 (0#, z1) 'switch to At theta=Theta0 ( )
Debug.Print "AX/Xt= "; AX/Xt; "Theta= "; theta
End Function
Private Function Theta0 ( ) As Double
Theta0=ModRegFall(0#,1#)
End Function
Private Function func1 (A As Double) As Double
func1=At*(1-A)/((1+(Xt-AX)*Kax)/Kad+Dt*(1-A))-A
End Function
Private Function func2 (B As Double) As Double
Dim T0 As Double
AX=B
T0=Theta0 ( )
func2=AT-AX-T0/(Kad*(1-T0))-T0*Dt
End Function
Private Function ModRegFall (XL As Double, X2 As Double)
As Double
'Modifie Regula Falsi'
'(adapted from Conte & de Boor, 1980)'
'Finds root of function func1, if bracketed'
Const xtol=0.000000000001
Const ftol=0.000000000000001
```

```
Const ntol=100
Dim SignF1 As Integer, n As Integer, PrvsF3 As Integer
Dim F1 As Double, F2 As Double, F3 As Double, X3 As
    Double
F1=func1 (X1)
F2=func1 (X2)
'test whether root is bracketed'
If Sgn (F1)*F2>0 Then
    Debug.Print "root not bracketed"
    Debug.Print "X1= ", X1, "X2= ", X2
    Debug.Print "func1 (X1)= ", F1, "func1 (X2)= ", F2
    End
End If
X3=X1
F3=F1
'BEGIN ITERATION'
For n=1 To ntol
'TEST FOR CONVERGENCE'
'Is interval small enough?'
If Abs (X1-X2)<=xtol Then
    ModRegFal1=X3
    Exit Function
End If
'Is F3 small enough?'
If Abs (F3)<=ftol Then
    ModRegFal1=X3
    Exit Function
End If
'GET NEW GUESS BY LINEAR INTERPOLATION'
X3=(F1*X2-F2*X1)/(F1-F2)
PrvsF3=Sgn (F3)
F3=func1 (X3)
'CHANGE TO NEW INTERVAL'
If Sgn (F1)*F3>=0 Then
    X1=X3
    F1=F3
    If F3*PrvsF3>=0 Then F2=F2/2#
Else
    X2=X3
    F2=F3
    If F3*PrvsF3>=0 Then F1=F1/2#
End If
Next n
'END ITERATION'
Debug.Print "X1= ", X1, "X2= ", X2, "X3= ", X3
Debug.Print "func1 (X1)= ", F1, "func1 (X2)= ", F2,"func1
    (X3)= ", F3
Debug.Print ntol, " iterations without convergence"
End Function
Private Function ModRegFal2 (Y1 As Double, Y2 As
    Double)
As Double
'Modified Regula Falsi'
'(adapted from Conte & de Boor, 1980)'
'Finds root of function func2, if bracketed'
Const xtol=0.000000000001
Const ftol=0.0000000001
Const ntol=100
Dim SignF1 As Integer, n As Integer, PrvsF3 As Integer
Dim F1 As Double, F2 As Double, F3 As Double, Y3 As
    Double
F1=func2(Y1)
F2=func2(Y2)
'test whether root is bracketed'
If Sgn (F1)*F2>0 Then
    Debug.Print "Y1= ", Y1, "Y2= ", Y2 Debug.Print "func2
        (Y1)=", F1, "func2(Y2)=", F2
    End
End If
Y3=Y1
F3=F1
'BEGIN ITERATION'
For n=1 To ntol
'TEST FOR CONVERGENCE'
'Is interval small enough?'
If Abs (Y1-Y2)<=xtol Then
    ModRegFal2=Y3
    Exit Function
End If
'Is F3 small enough?'
If Abs (F3)<=ftol Then
    ModRegFal2=Y3
    Exit Function
End If
'GET NEW GUESS BY LINEAR INTERPOLATION'
Y3=(F1*Y2-F2*Y1)/(F1-F2)
Prvs3=Sgn(F3)
F3=func2(Y3)
'CHANGE TO NEW INTERVAL'
If Sgn (F1)*F3>=0 Then
    Y1=Y3
    F1=F3
    If F3*PrvsF3>=0 Then F2=F2/2#
Else
    Y2=Y3
    F2=F3
    If F3*PrvsF3>=0 Then F1=F1/2#
End If
Next n
'END ITERATION'
Debug.Print "Y1= ", YL, "Y2= ", Y2, "Y3= ", Y3
Debug.Print "func2(Y1)= ", F1, "func2(Y2)= ", F2, "func2
    (Y3)= ",F3
Debug.Print ntol, " iterations without convergence"
End Function
```

EXAMPLE 7

Application of the Fret Competition Assay to Characterize the Impact of Base Mismatches and Adducts on DNA Duplex Thermodynamic Stability (I) Base Substitutions (Mismatches)

Using the novel FRET competition assay, the thermodynamic stability of DNA duplexes containing single nucleotide polymorphisms (SNPs) has been characterized. Oligonucleotides comprising 13-mer sequence fragments from the ApoE gene, each containing a single SNP site (e.g., 112), have been synthesized, purified and post-synthesis labeled with fluorescent probes. The resultant duplexes contain a pair of fluorophores, each located on one of the 5'-ends, with the property of acting as a donor/acceptor pair in fluorescence energy transfer assays. Each SNP site has been studied using both the parent common allele sequence (e.g., 13-mer containing CAC/GTG) and the variant form (e.g., 13-mer containing CGC/GCG) in the center. The corresponding unlabeled oligonucleotides have been used in the competition experiments, revealing that this sensitive method facilitates distinction of the common versus variant sequence, based on a significant difference in free energy values. The FRET duplexes have also been challenged with longer fragments (e.g., 50-mers) containing the 13-mer regions centered and flanked by the naturally occurring sequences of the ApoE gene. The results tabulated below (Table 1) reveal that within experimental error, determination of the free energy ($\Delta G°$) and differences in stability ($\Delta\Delta G°$) are not significantly influenced by the length of the competitor sequence. The accuracy of the FRET measurements are therefore not compromised by the presence of overhanging bases and/or possible competing alternate structures that often occur within longer DNA fragments. It is interesting to note that the $\Delta G°$ and $\Delta\Delta G°$ for the SNP variant are fingerprints for this particular base mismatch, as the nature of the base substitution/mismatch and sequence context are primary determinants of DNA duplex thermodynamic stability.

TABLE 1

Competitive equilibria-derived $\Delta G°$ and $\Delta\Delta G°$ for the Parent and Cys[112]Arg Substituted 13- and 50-mer DNA Duplex Fragments of Apolipoprotein E.

| Duplex Core | Base Pair | 13-mer $\Delta G°$ (kcal/mol) | 13-mer $\Delta\Delta G°$ (kcal/mol) | 50-mer $\Delta G°$ (kcal/mol) | 50-mer $\Delta\Delta G°$ (kcal/mol) |
|---|---|---|---|---|---|
| -CAC-<br>-GTG- | A•T | −10.0 | N/A | −9.3 | N/A |
| -CAC-<br>-GCG- | A•C | −7.1 | −2.9 | −6.6 | −2.7 |

(II) Cisplatin versus Oxaliplatin Adducts

Platinum complexes have been used clinically for the suppression of tumor growth for several decades. The anticancer effect of cisplatin arises from its ability to form covalent cross-links of adjacent purines in DNA, the major adduct comprising the 1,2-d(GpG) intrastrand cross-link. Due to its lack of cross-resistance and greater cytotoxicity, oxaliplatin, a newer generation platinum-derived anticancer drug, recently has been selected as the preferred choice against numerous types of cancer. The impact of platinum compounds has been studied extensively by structural and thermodynamic approaches, revealing that in spite of the presence of non-leaving groups, oxaliplatin imparts minimal additional effects relative to cisplatin on the microscopic properties of the host duplexes. To correlate the structure and thermodynamics of the adduct-modified DNA duplexes, the 12-mer oligonucleotide sequence

[d(CCTCTGGTCTCC)•d(GGAGACCAGAGG)], (SEQ ID NO: 4)

employed in the X-ray crystallographic studies that have been reported previously for cisplatin and oxaliplatin, has been selected.

The energetic consequence of incorporating either cisplatin or oxaliplatin adducts at the central d(GpG) position in the host 12-mer DNA duplex has been assessed by a combination of calorimetric and spectroscopic techniques, including the FRET competition assay. The latter methodology employs a competitive equilibrium titration coupled with fluorescence energy detection that offers several unique advantages relative to conventional spectroscopic and calorimetric techniques. These include the direct, isothermal determination of differential energetic stability, while effectively abrogating single strand effects. Consequently, the FRET assay permits characterization of the energetic impact of cisplatin or oxaliplatin adducts in a single isothermal titration experiment. The results of the FRET competition assays reveal that the cisplatin and oxaliplatin adducts thermodynamically destabilize the host duplex (Table 2). Interestingly, the presence of the nonpolar carrier ligand (as in the oxaliplatin adduct) does not further destabilize the host duplex when compared with cisplatin, since the magnitude of destabilization is essentially identical for both adducts within experimental error. These findings are corroborated by the calorimetric and spectroscopic techniques, which demonstrate that the impact of both adducts are nearly identical.

TABLE 2

Competitive equilibria-derived $\Delta G°$ and $\Delta\Delta G°$ for the Canonical and Adduct-Containing Cisplatin (G^G) and Oxaliplatin (G♦G) 12-mer DNA Duplexes.

| Duplex Core | $\Delta G°$ (kcal/mol) | $\Delta\Delta G°$ (kcal/mol) |
|---|---|---|
| GG | −13.3 | N/A |
| G^G | −10.8 | −2.5 |
| G♦G | −11.0 | −2.3 |

The overall results underscore the utility of FRET competition assays for characterizing the impact of a defect on DNA duplex free energies in a manner that directly accounts for single strand effects and thereby precludes measurement of heat capacity changes, the latter often neglected when calorimetric/optical methods are employed. The FRET competition assay therefore represents a method of choice both in terms of complementing conventional thermal denaturation studies, and providing a direct measure of the differential thermodynamic stability in the absence of single strand stacking/self-structure.

EXAMPLE 8

Catalyst/Inhibitor System for Detecting Duplexes

Alkaline phosphatase is used widely in detection of hybridization events, usually conjugated to an antibody. A number of thermally tolerant alkaline phosphatases are available as are a variety of detection schemes, which taken together make the enzyme attractive for our competitive equilibrium method. A number of protocols for conjugation of the enzyme with oligodeoxynucleotides have been described (Jablonski, E., et al. (1986) Nucl. Acids Res. 14:6115-6128; Ghosh, S. S., et al. (1990) Bioconjugate Chem. 1:71-76; Thuong and Asseline (2000) Current Protocols in Nucleic Acid Chemistry, 4.2.1-4.2.33). Of the available conjugation methods, the methods described below are preferred based on their relative simplicity and on the production of thermally stable conjugates. A variety of colorogenic and fluorogenic substrates are available commercially for detection of alkaline phosphatase; in general, removal of inorganic phosphate from the substrates results in production of an absorbent or fluorescent alcohol. Examples include p-nitrophenyl phosphate (absorbance detection) and 2'[2-benzothiazoyl]-6'-hydroxybenzothiazole phosphate (AttoPhos® AP Fluorescent Substrate System, Promega, Madison, Wis.). Given the high extinction coefficients of the fluorescent reporter molecule, a detection limit is anticipated on the order of attomoles of active alkaline phosphatase.

Theophylline (1,3-dimethylxanthine), a clinically important bronchodilator, is a noncompetitive inhibitor of alkaline phosphatase (McComb, R. B., et al. (1979) Alkaline Phosphatase, Plenum Press, New York). The conjugation of theophylline to an oligonucleotide via an appropriate linker should produce potent inhibition of alkaline phosphatase conjugated to a complementary oligonucleotide. Because theophylline is a noncompetitive inhibitor, substrate will bind to the enzyme-inhibitor complex in the duplex; however, the amount bound will not be significant in terms of the measured quantities. Other methylxanthines do not inhibit alkaline phosphatase activity (McComb, R. B., et al. (1979) Alkaline Phosphatase, Plenum Press, New York), suggesting that the lack of a substituent at the 7 position is important for inhibition. Linkage between theophylline and the oligonucleotide can be made via the 1 or 3 methyl moiety. Use of a terminal 1,3-dimethylxanthosine may permit easier synthesis of the inhibitor complex. However, formation of the glycosidic bond and the accompanying deprotonation at N7, are likely to interfere with the enzyme inhibition.

A variety of coupling chemistries can be exploited to attach proteins and small molecules to oligonucleotides (Thuong and Asseline (2000) Current Protocols in Nucleic Acid Chemistry, 4.2.1-4.2.33; Davies, M. J., et al. (2000) Chem. Soc. Rev. 29:97-107). In the following description, the inhibitor is attached at the 3' end and the catalyst at the 5' end of their respective oligonucleotides; this orientation is in not necessitated by the competitive equilibrium method or by the properties of the enzyme or the inhibitor and may be reversed. The proposed orientation merely provides for convenience in the synthesis of the linker-modified oligonucleotides.

Attachment of a modified theophylline at the 3' end of an oligonucleotide can be effected via coupling to a linker terminated in a primary amine. The oligonucleotide can be synthesized using the 2'-deoxycytidine, 3'-succinoyl-long chain alkylamino-CPG [5'-Dimethoxytrityl-N-dimethylformamidine-5-[N-(trifluoroacetylaminohexyl)-3-acrylimido]] (Glen Research; Sterling, Va.). Modifications to the standard synthetic procedures may not be required for incorporation of an amino linker at the 3' end of the oligonucleotide using this controlled pore glass-linked phosphoramidate. A succinimido ester-linked theophylline derivative can be synthesized. Because caffeine (1,3,7-trimethylxanthine) does not inhibit the enzyme, obstruction of the N7 position is likely to interfere with alkaline phosphatase inhibition. Therefore, linkage may be via either the N1 or N3 position. An excess of the resultant succinimido ester-linked theophylline may be incubated with the amino-linker modified oligonucleotide at room temperature to form the oligonucleotide-inhibitor conjugate, I.

The oligonucleotide-catalyst conjugate will be prepared using the 5'-Thiol-Modifier C6 [(S-Trityl-6-mercaptohexyl)-(2-cyanoethyl)-(N,N-diisopropyl)-phosphoramidite] (Glen Research). The production of thiolated oligonucleotides may require minor modifications of the standard synthesis protocols for the final steps of the oligonucleotide synthesis. The oxidation step in the final cycle of synthesis may use 0.02M iodine solution to minimize oxidative cleavage of the trityl-S-linkage and the trityl group protecting the sulfur must be removed with silver nitrate. Alkaline phosphatase can be modified by incorporation of maleimide groups (Ghosh, S. S., et al. (1990) Bioconjugate Chem. 1:71-76). The enzyme may be treated with a 50-fold excess of the heterobifunctional linker 6-maleimidohexanoic acid succinimido ester (MHS). Reaction at room temperature for 30 min can produce the maleimide modified enzyme. An average of about 6 maleimide residues per enzyme can be expected (Ghosh, S. S., et al. (1990) Bioconjugate Chem. 1:71-76). Coupling of the modified enzyme to the thiolated oligonucleotide may be accomplished by incubation of a 5-fold excess of enzyme with oligonucleotide for 16 hours at room temperature. The resultant complex can be separated from unreacted enzyme/oligonucleotides by gel filtration.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for screening for nucleic acid duplex stability by competitive equilibria comprising:
   (a) providing a solution comprising a known amount of an initial nucleic acid duplex with a known stability, said initial nucleic acid duplex comprising a first nucleic acid strand having a sequence wholly or in part homologous to a target strand of a target nucleic acid molecule and a second nucleic acid strand having a sequence wholly or in part complementary to said target strand of said target nucleic acid molecule; and
   (b) titrating said solution with a second solution comprising a known concentration of said target nucleic acid molecule, wherein said target nucleic acid molecule is single- or double-stranded, and wherein said titration comprises:
   (i) adding said second solution to the solution of step (a);
   (ii) subjecting the solution generated in step (i) to conditions which disrupt said initial nucleic acid duplex of step (a) and any duplex or triplex formed in step (i) between said target strand and said second nucleic acid strand of said initial nucleic acid duplex of step (a), but which do not disrupt said target nucleic acid molecule when double-stranded;
   (iii) subjecting the solution generated in step (ii) to conditions which promote duplex or triplex formation; and
   (iv) monitoring the solution of step (iii) for changes in the amount of initial nucleic acid duplex formed as a function of the amount of target nucleic acid molecule added, thereby determining the stability of the nucleic acid duplex or triplex formed in step (iv) comprising the target nucleic acid molecule and the second nucleic acid strand of the initial nucleic acid duplex of step (a).

2. The method of claim 1 wherein the conditions in step (ii) comprise heating said solution and the conditions of step (iii) comprise cooling said solution.

3. A method for screening for nucleic acid duplex stability comprising:
   (a) providing a solution comprising an initial nucleic acid duplex with a known stability, said initial nucleic acid duplex comprising a first nucleic acid strand and a second nucleic acid strand, each strand being capable of forming a duplex with a strand from a double-stranded target nucleic acid molecule; and
   (b) titrating a solution comprising said target nucleic acid molecule into the solution of step (a), wherein said titration comprises:
   (i) adding the solution comprising the target nucleic acid molecule to the solution of step (a);
   (ii) subjecting the solution generated in step (i) to conditions which disrupt said initial nucleic acid duplex of step (a), said double-stranded target strand, and any duplex between a strand of the disrupted target nucleic acid molecule and the first and second nucleic acid strands said initial nucleic acid duplex of step (a);
   (iii) subjecting the solution generated in step (ii) to conditions which promote duplex formation; and
   (iv) monitoring the solution of step (iii) for changes in the amount of initial nucleic acid duplex formed as a function of the amount of target nucleic acid molecule added, thereby determining the stability of said nucleic acid duplex.

4. The method of claim 3 wherein the conditions in step (ii) comprise heating the solution and the conditions of step (iii) comprise cooling the solution.

5. A method for extracting enthalpy data from the competitive equilibria method of claim 2 comprising controlling the temperature decrease during step (iii) so that changes monitored in step (iv) can be collected as a function of temperature to produce titration curves that can be used to extract enthalpy ($\Delta H°$) data.

6. A method for extracting enthalpy data from the competitive equilibria method of claim 4 comprising controlling temperature decrease during step (iii) so that changes monitored in step (iv) can be collected as a function of temperature to produce titration curves that can be used to extract enthalpy ($\Delta H°$) data.

7. A method for detecting at least one single nucleotide polymorphism comprising:
   (a) providing a solution comprising a known amount of an initial nucleic acid duplex comprising a first and second nucleic acid strand, wherein said first or second strand of the duplex is designed to identify at least one single nucleotide polymorphism in a single- or double-stranded target nucleic acid molecule;

(b) adding a fixed excess amount of said target nucleic acid molecule to said solution;

(c) subjecting said solution to conditions which disrupt said initial nucleic acid duplex of step (a) and any duplex or triplex formed between a strand of said target nucleic acid molecule and said first or second nucleic acid strand of said initial nucleic acid duplex of step (a), but which do not disrupt the target strand when double-stranded;

(d) subjecting said solution to conditions which promote duplex or triplex formation; and (e) measuring the amount of initial duplex formed after addition of the target nucleic acid molecule wherein the measured amount after addition of the target nucleic acid molecule is indicative of the target nucleic acid molecule containing said at least one single nucleotide polymorphism.

8. The method of claim 7 wherein the conditions in step (c) comprise heating said solution and the conditions of step (d) comprise cooling said solution.

9. A method for detecting at least one single nucleotide polymorphism comprising:

(a) providing a solution comprising a known amount of an initial nucleic acid duplex comprising a first and second nucleic acid strand, wherein said first or second strand of the duplex is designed to identify at least one single nucleotide polymorphism in a double-stranded target nucleic acid molecule;

(b) adding a fixed excess amount of said double-stranded target nucleic acid molecule into the solution;

(c) subjecting said solution to conditions which disrupt said initial nucleic acid duplex, said double-stranded target nucleic acid molecule, and any duplex formed between a strand of said double-stranded target nucleic acid molecule and said first or second nucleic acid strand of said initial nucleic acid duplex of step (a);

(d) subjecting said solution to conditions which promote duplex formation; and (e) measuring the amount of initial duplex formed after addition of said double-stranded target nucleic acid molecule wherein the measured amount after addition of the target strand is indicative of said double-stranded target nucleic acid molecule containing said at least one single nucleotide polymorphism.

10. The method of claim 9 wherein the conditions in step (c) comprise heating said solution and the conditions of step (d) comprise cooling said solution.

11. The method of claim 7 wherein one strand of the initial nucleic acid duplex of step (a) contains a sequence corresponding to the at least one single nucleotide polymorphism of said target nucleic acid molecule; and wherein said measured amount of initial duplex formed after addition of the target nucleic acid molecule indicative of the target nucleic acid molecule containing the at least one single nucleotide polymorphism in step (e) decreases as compared to said amount in step (a).

12. The method of claim 9 wherein one strand of the initial nucleic acid duplex of step (a) contains a sequence corresponding to the at least one single nucleotide polymorphism of said target nucleic acid molecule; and wherein said measured amount of initial duplex formed after addition of the target nucleic acid molecule indicative of the target nucleic acid molecule containing the at least one single nucleotide polymorphism in step (e) decreases as compared to said amount in step (a).

13. The method of claim 7 wherein one strand of the initial nucleic acid duplex of step (a) is a wild type sequence; and wherein said measured amount of initial duplex formed after addition of the target nucleic acid molecule is indicative of the target nucleic acid molecule containing said at least one single nucleotide polymorphism in step (e) is approximately equal to said known amount in step (a).

14. The method of claim 9 wherein one strand of the initial nucleic acid duplex of step (a) is a wild type sequence; and wherein said measured amount of initial duplex formed after addition of the target nucleic acid molecule is indicative of the target nucleic acid molecule containing said at least one single nucleotide polymorphism in step (e) is approximately equal to said known amount in step (a).

15. A method for determining the concentration of a target nucleic acid molecule comprising:

(a) contacting a known volume and concentration of an initial nucleic acid duplex with a known stability and a known volume of a solution containing a target nucleic acid molecule, wherein said initial nucleic acid duplex comprising a first nucleic acid strand having a sequence wholly or in part homologous to a target strand of said target nucleic acid molecule and a second nucleic acid strand having a sequence wholly or in part complementary to said target strand of said target nucleic acid molecule;

(b) subjecting the solution to conditions which disrupt the initial nucleic acid duplex and any duplex between a strand of the target nucleic acid molecule and a strand of the initial nucleic acid duplex of step (a);

(c) subjecting said solution to conditions which promote duplex formation; and (d) determining the relative change in the amount of initial duplex formed in the solution, thereby determining the concentration of said target nucleic acid molecule.

16. The method of claim 15 wherein the conditions in step (b) comprise heating said solution and the conditions of step (c) comprise cooling said solution.

17. A method for assessing stability of various selected target nucleic acid molecules comprising:

(a) selecting various target nucleic acid molecules;

(b) performing the method of claim 1 with the same initial nucleic acid duplex and each of the selected target nucleic acid molecules; and (c) comparing monitored changes in the amount of initial nucleic acid duplex formed as a function of the amount of the selected target nucleic acid molecule added to ascertain differences in stability of duplexes or triplexes formed by the various target nucleic acid molecules.

18. The method of claim 1 wherein said first strand of said initial nucleic acid duplex of step (a) is linked to a first member of a specific binding pair and said second strand of said initial nucleic acid duplex of step (a) is linked to a second member of said specific binding pair.

19. The method of claim 3 wherein said first strand of said initial nucleic acid duplex of step (a) is linked to a first member of a specific binding pair and said second strand of said initial nucleic acid duplex of step (a) is linked to a second member of said specific binding pair.

20. The method of claim 7 wherein said first strand of said initial nucleic acid duplex of step (a) is linked to a first member of a specific binding pair and said second strand of said initial nucleic acid duplex of step (a) is linked to a second member of said specific binding pair.

21. The method of claim 9 wherein said first strand of said initial nucleic acid duplex of step (a) is linked to a first member of a specific binding pair and said second strand of said initial nucleic acid duplex of step (a) is linked to a second member of said specific binding pair.

22. The method of claim 15 wherein said first strand of said initial nucleic acid duplex of step (a) is linked to a first member of a specific binding pair and said second strand of said initial nucleic acid duplex of step (a) is linked to a second member of said specific binding pair.

23. The method of claim 17 wherein said first strand of said initial nucleic acid duplex of step (a) is linked to a first member of a specific binding pair and said second strand of said initial nucleic acid duplex of step (a) is linked to a second member of said specific binding pair.

24. The method of claim 1 wherein at least one nucleic acid strand of the initial duplex comprises an internal loop, a modified base, a modified backbone, or a non-Watson-Crick nucleotide base variation.

25. The method of claim 3 wherein at least one nucleic acid strand of the initial duplex comprises an internal loop, a modified base, a modified backbone, or a non-Watson-Crick nucleotide base variation.

26. The method of claim 7 wherein at least one nucleic acid strand of the initial duplex comprises an internal loop, a modified base, a modified backbone, or a non-Watson-Crick nucleotide base variation.

27. The method of claim 9 wherein at least one nucleic acid strand of the initial duplex comprises an internal loop, a modified base, a modified backbone, or a non-Watson-Crick nucleotide base variation.

28. The method of claim 15 wherein at least one nucleic acid strand of the initial duplex comprises an internal loop, a modified base, a modified backbone, or a non-Watson-Crick nucleotide base variation.

29. The method of claim 17 wherein at least one nucleic acid strand of the initial duplex comprises an internal loop, a modified base, a modified backbone, or a non-Watson-Crick nucleotide base variation.

30. The method of claim 1 wherein at least one nucleic acid strand of the initial nucleic acid duplex is immobilized to a solid support.

31. The method of claim 3 wherein at least one nucleic acid strand of the initial nucleic acid duplex is immobilized to a solid support.

32. The method of claim 7 wherein at least one nucleic acid strand of the initial nucleic acid duplex is immobilized to a solid support.

33. The method of claim 9 wherein at least one nucleic acid strand of the initial nucleic acid duplex is immobilized to a solid support.

34. The method of claim 15 wherein at least one nucleic acid strand of the initial nucleic acid duplex is immobilized to a solid support.

35. The method of claim 17 wherein at least one nucleic acid strand of the initial nucleic acid duplex is immobilized to a solid support.

36. The method of claim 30 wherein changes in the amount of initial nucleic acid duplex formed are monitored via surface plasmon resonance spectroscopy.

37. The method of claim 31 wherein changes in the amount of initial nucleic acid duplex formed are monitored via surface plasmon resonance spectroscopy.

38. The method of claim 32 wherein changes in the amount of initial nucleic acid duplex formed are monitored via surface plasmon resonance spectroscopy.

39. The method of claim 33 wherein changes in the amount of initial nucleic acid duplex formed are monitored via surface plasmon resonance spectroscopy.

40. The method of claim 34 wherein changes in the amount of initial nucleic acid duplex formed are monitored via surface plasmon resonance spectroscopy.

41. The method of claim 35 wherein changes in the amount of initial nucleic acid duplex formed are monitored via surface plasmon resonance spectroscopy.

42. The method of claim 18 wherein said specific binding pair is selected from the group consisting of antibody and antigen; enzyme and inhibitor; enzyme and coenzyme; and catalyst and inhibitor.

43. The method of claim 19 wherein said specific binding pair is selected from the group consisting of antibody and antigen; enzyme and inhibitor; enzyme and coenzyme; and catalyst and inhibitor.

44. The method of claim 20 wherein said specific binding pair is selected from the group consisting of antibody and antigen; enzyme and inhibitor; enzyme and coenzyme; and catalyst and inhibitor.

45. The method of claim 21 wherein said specific binding pair is selected from the group consisting of antibody and antigen; enzyme and inhibitor; enzyme and coenzyme; and catalyst and inhibitor.

46. The method of claim 22 wherein said specific binding pair is selected from the group consisting of antibody and antigen; enzyme and inhibitor; enzyme and coenzyme; and catalyst and inhibitor.

47. The method of claim 23 wherein said specific binding pair is selected from the group consisting of antibody and antigen; enzyme and inhibitor; enzyme and coenzyme; and catalyst and inhibitor.

\* \* \* \* \*

SEQUENCE LISTING

<160> NUMBER OF SEQ ID NOS: 4

<210> SEQ ID NO 1
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 1
gcgtacacat gcg                                                        13

<210> SEQ ID NO 2
<211> LENGTH: 13
<212> TYPE: DNA
<213> ORGANISM: Artificial Sequence
<220> FEATURE:
<223> OTHER INFORMATION: Synthetic Sequence

<400> SEQUENCE: 2
cgcatgtgta cgc                                                        13

<210> SEQ ID NO 3

-continued

```
<211> LENGTH: 13
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (7)...(7)
<223> OTHER INFORMATION: n = abasic furan

<400> SEQUENCE: 3
cgcatgngta cgc                                                          13

<210> SEQ ID NO 4
<211> LENGTH: 12
<212> TYPE: DNA
<213> ORGANISM: Artificial Sequence
<220> FEATURE:
<223> OTHER INFORMATION: Synthetic Sequence

<400> SEQUENCE: 4
cctctggtct cc                                                           12
```